United States Patent
Melenski et al.

(10) Patent No.: US 11,325,883 B2
(45) Date of Patent: May 10, 2022

(54) FUNCTIONALIZED N,N-DIALKYLAMINO PHENYL ETHERS AND THEIR METHOD OF USE

(71) Applicant: Temple University—Of The Commonwealth System of Higher Education, Philadelphia, PA (US)

(72) Inventors: Edward G. Melenski, Royersford, PA (US); Wayne E. Childers, New Hope, PA (US); Marlene A. Jacobson, Melrose Park, PA (US); Magid A. Abou-Gharbia, Exton, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 204 days.

(21) Appl. No.: 16/764,424

(22) PCT Filed: Nov. 20, 2018

(86) PCT No.: PCT/US2018/061911
§ 371 (c)(1),
(2) Date: May 15, 2020

(87) PCT Pub. No.: WO2019/103989
PCT Pub. Date: May 31, 2019

(65) Prior Publication Data
US 2020/0354307 A1  Nov. 12, 2020

Related U.S. Application Data

(60) Provisional application No. 62/589,574, filed on Nov. 22, 2017.

(51) Int. Cl.
| | | |
|---|---|---|
| *C07C 225/16* | (2006.01) | |
| *A61K 31/138* | (2006.01) | |
| *A61P 3/00* | (2006.01) | |
| *C07C 49/255* | (2006.01) | |
| *A61P 31/10* | (2006.01) | |

(52) U.S. Cl.
CPC .......... *C07C 225/16* (2013.01); *A61K 31/138* (2013.01); *A61P 3/00* (2018.01); *C07C 49/255* (2013.01); *A61P 31/10* (2018.01)

(58) Field of Classification Search
CPC ... C07C 217/22; C07C 225/16; C07C 49/255; A61K 31/135; A61K 31/138; A61P 3/00; A61P 31/10
See application file for complete search history.

(56) References Cited

U.S. PATENT DOCUMENTS

| | | |
|---|---|---|
| 4,623,660 A | 11/1986 | Richardson |
| 6,489,481 B1 | 12/2002 | Keith et al. |
| 6,875,775 B2 | 4/2005 | Soedervall |
| 7,423,181 B2 | 9/2008 | Nielsen |
| 2012/0129860 A1 | 5/2012 | Scott |
| 2014/0005168 A1 | 1/2014 | Do |

FOREIGN PATENT DOCUMENTS

| | | |
|---|---|---|
| WO | 1998050343 | 11/1998 |
| WO | 2000006085 | 2/2000 |
| WO | 2010033643 | 3/2010 |
| WO | 2016050921 | 4/2016 |
| WO | 2017205451 | 11/2017 |

OTHER PUBLICATIONS

Jeyakumar, M. et al., "Storage solutions: Treating lysosomal disorders of the brain," Nat. Rev. Neuro., 2005, 6:1-12.
Meikle, P. J., et al., "Prevalence of lysosomal storage diseases," JAMA, 1999, 281: 249 -254.
Horowitz, M. et al., "Mutations causing Gaucher disease," Hum. Mutat., 1994, 3: 1-11.
Grabowski G. A., "Gaucher disease and other storage disorders," Hematology Am. Soc. Hematol. Educ. Program, 2012;13-18.
Desnick, R. J. et al., "Enzyme replacement and enhancement therapies: lessons from lysosomal disorders," Nat Rev. Genet., 2002, 3:954-966.
Zheng, W. et al., "Three classes of glucocerebrosidase inhibitors identified by quantitative high-throughput screening are chaperone leads for Gaucher disease," Proc. Natl. Acad. Sci. USA, 2007, 104: 13192-13197.
Koltun, E. et al., "Discovery of a new class of glucosylceramide synthase inhibitors," Bioorg. Med. Chem. Lett., 2011, 21: 6773-6777.
Larsen, S. D. et al., "Property-based design of glucosylceramide synthase inhibitor that reduces glucosylceramide in the brain," J. Lipid Res., 2012, 53:282-291.
Stone, D. L. et al., "Glucocerebrosidase gene mutations in patients with type 2 Gaucher disease," Hum. Mutat., 2000, 15:181-8.
Sawkar, A. R. et al., "Gaucher disease-associated glucocerebrosidases show mutation-dependent chemical chaperoning profiles," Chem. Biol., 2005, 12: 1235-1244.
Swinney, D. C., "The Contribution of Mechanistic Understanding to Phenotypic Screening for First-in-Class Medicines Phenotypic assays in drug discovery," J. Biomol. Screen, 2013, 18:1186-1192.
Lloyd-Evans, E. et al., "Niemann-Pick disease type C1 is a sphingosine storage disease that causes deregulation of lysosomal calcium," Nat. Med., 2008,14: 1247-55.
Kilpatrick, B. S. et al., "Endoplasmic reticulum and lysosomal Ca+2 stores are remodeled in GBA1-Linked Parkinson's disease and patient fibroblasts," Cell Calcium, 2016, 59:12-20.
Lloyd-Evans, E. et al., "Lysosomal Ca(2+) homeostasis: role in pathogenesis of lysosomal storage diseases," Cell Calcium, 2011, 50:200-205.
Morgan, A. J. et al., "Molecular mechanism of endolysosomal Ca2+ signaling in health and disease," Biochem. J., 2011, 439:349-374.

(Continued)

*Primary Examiner* — Theodore R. Howell
(74) *Attorney, Agent, or Firm* — Riverside Law LLP

(57) ABSTRACT

Pharmaceutical compositions of the invention comprise functionalized N,N-dialkylamino phenyl ethers derivatives having a disease-modifying action in the treatment of diseases associated with lysosomal storage dysfunction that include Gaucher's disease, and any disease or condition involving lysosomal storage dysfunction.

16 Claims, 7 Drawing Sheets

(56) References Cited

OTHER PUBLICATIONS

Sidransky, E. et al., "The link between the GBA gene and parkinsonism," Lancet Neurol, 2012, 11:986-998.

Schapira, A. et al., "The relationship between glucocerebrosidase mutations and Parkinson disease," J. Neurochem., 2016, 139(supplement 1):77-90.

Wang, F. et al., "Lacidipine Remodels Protein Folding and Ca2+ Homeostasis in Gaucher's Disease Fibroblasts: A Mechanism to Rescue Mutant Glucocerebrosidase," Chem. Biol., 2011, 18:766-776.

Mu, T.-W. et al., "Partial Restoration of Mutant Enzyme Homeostasis in Three Distinct Lysosomal Storage Disease Cell Lines by Altering Calcium Homeostasis," PLoS Biol., 2008, 6:e26.

Ong, D. S. T. et al., "Endoplasmic Reticulum Ca2+ Increases Enhance Mutant Glucocerebrosidase Proteostasis," Nat. Chem. Biol., 2010, 6:424-432.

Witte, M. D. et al., "Ultrasensitive in situ visualization of active glucocerebrosidase molecules," Nat. Chem. Biol., 2010, 6:907-913.

Jian, J. et al., "Progranulin Recruits HSP70 to β-Glucocerebrosidase and is Therapeutic Against Gaucher Disease," EBioMedicine, 2016 13:212-224.

FUNCTIONALIZED N,N-DIALKYLAMINO PHENYL ETHERS AND THEIR METHOD OF USE

CROSS-REFERENCE TO RELATED APPLICATIONS

This application is a U.S. national phase application filed under 35 U.S.C. 371 claiming benefit to International Application No. PCT/US2018/061911, filed Nov. 20, 2018, which claims priority to U.S. Provisional Application Ser. No. 62/589,574, filed Nov. 22, 2017. The entire contents of all of the above applications are incorporated by reference herein in their entireties.

FIELD OF INVENTION

The present invention describes novel functionalized N,N-dialkylamino phenyl ethers as well as compositions and their methods of use to prevent and/or treat lysosomal storage disorders and related conditions. The present invention further describes a novel chemotype useful for the treatment of Gaucher's disease, Tay-Sachs disease, Sandhoff's disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, GM2 gangliosidosis, and other diseases that involve dysfunction of lysosomal storage.

BACKGROUND OF THE INVENTION

Lysosomal storage disorders (LSDs) are inheritable metabolic diseases with deficiencies in enzymes that function within the glycosphingolipid biosynthetic and metabolic pathway. As a consequence, non-degraded substrates accumulate and normal lysosome function is compromised, resulting in cell enlargement, impaired autophagy, disruption of cell signaling and eventually cell death. Two thirds of LSDs have central nervous system involvement resulting in a progressive neurodegeneration and the leading cause of patient death (Jeyakumar, M, Dwek, R A, Butters, T D and Platt, F M. (2005) Storage solutions: Treating lysosomal disorders of the brain, Nat Rev Neuro 6:1-12.). A group of more than 50 diseases have been classified as LSDs, including Gaucher, Tay-Sachs, Sandhoff and Fabry disease, Niemann-Pick type C and GM1 gangliosidosis. The overall prevalence is 1 in every 7700 births. With the exception of Gaucher Type 1, there are no effective treatments for these diseases. The most common lysosomal storage disorder is the autosomal recessive Gaucher disease, with a prevalence of 1 in 57,000 births (Meikle, P J, Hopwood, J J, Clauge, W F and Carery, W F. (1999) Prevalence of lysosomal storage diseases JAMA 281: 249-254.). A high carrier rate exists within Jewish populations of Eastern European decent with a corresponding incidence of 1 in 500 of affected individuals [Horowitz M. and Zimran A. (1994) Mutations causing Gaucher disease. Hum. Mutat. 3: 1-11.).

Gaucher disease is associated with a deficiency in the enzyme β-glucocerebrosidase (GCase) due to mutations of the GBA1 gene and leads to accumulation of its substrate, glucosylceramide. The most prevalent mutations are N370S and L444P. Gaucher Type 1 clinical features include hepatomegaly, splenomegaly, anemia, thrombocytopenia and bone lesions (Grabowski G A, Gaucher disease and other storage disorders. (2012) Hematology Am Soc Hematol Educ Program, 2012; 13-18.). To overcome the deficiency, enzyme replacement therapy (ERT) with administration of recombinant glucocerebrosidase (Cerezyme), has had a significant impact on the treatment of Gaucher disease (Desnick, R J and Schuchman, E H. (2002) Enzyme replacement and enhancement therapies: lessons from lysosomal disorders, Nat Rev. Genet. 3:954-966.), however its effectiveness is limited to patients with non-neuronopathic, or Type 1 Gaucher, due to the inability of the enzyme to cross the blood-brain barrier. The neuronopathic forms of Gaucher disease, associated with L444P homozygotes or compound homozygotes, are classified according to the onset and severity of disease symptoms. Type 3 (subacute juvenile or early adult onset) can begin anytime, and patients can live into early teens or adulthood. Type 2 (acute infantile onset), begins within 6 months of birth, rapidly progresses and is fatal, usually within two years of age (Grabowski G A, Gaucher disease and other storage disorders. (2012) Hematology Am Soc Hematol Educ Program, 2012; 13-18.). ERT has limited efficacy for Gaucher Type 3 disease where mild CNS symptoms are present, and for patients with Gaucher Type 2 disease and severe brain pathologies, ERT shows no efficacy. Detection by newborn screening and early treatment would improve the prognosis for these patients; however, there are no current treatment options to support testing inclusion.

The application of high throughput screening (HTS) approaches to identify small molecule treatments for LSDs has targeted specific enzymes with biochemical assays designed to either identify chaperones for the known defective enzymes (Zheng W, Padia J, Urban D J, Jadhav A, Goker-Alpan O, et al. (2007) Three classes of glucocerebrosidase inhibitors identified by quantitative high-throughput screening are chaperone leads for Gaucher disease. Proc Natl Acad Sci USA 104: 13192-13197.) and/or compounds to clear accumulating substrates resulting from decreased activity of the mutated enzyme (Koltun E, Richards S, Chan V, Nachtigall J, Du H, Noson K, Galan A, Aay N, Hanel A, Harrison A, Zhang J, Won K A, Tam D, Qian F, Wang T, Finn P, Ogilvie K, Rosen J, Mohan R, Larson C, Lamb P, Nuss J and Kearney P (2011) Discovery of a new class of glucosylceramide synthase inhibitors. Bioorg Med Chem Lett. 21: 6773-6777.). Because HTS employs chemical libraries, this strategy has the potential to identify candidates suitable for optimizing physicochemical properties to achieve therapeutic exposures in the brain and develop oral treatments for neuronopathic Gaucher disease. Eliglustat (Cerdelga™) and Miglustat (Zavesca®), compounds targeting inhibition of glucosylceramide synthase to reduce accumulating substrates, have received FDA approval, however both drugs fail to achieve CNS exposures and are limited to only treating Gaucher Type 1 (Larsen, S D, Wilson, M W, Abe, A., Shu, L, George, G H, Kirchoff, P, Hollis Showalter, H D, Xiang, J, Keep, R F and Shayman, J A. (2012) Property-based design of glucosylceramide synthase inhibitor that reduces glucosylceramide in the brain, J. Lipid Res. 53:282-291.). Another approach is to develop small molecules as chemical chaperones to assist misfolded mutant GCase and enhance stability; however, there is substantial heterogeneity within neuronopathic Gaucher disease Type 2 and a single small molecule might not function as a chaperone for all genotypes (Stone, D L, Tayebi N, Orvisky E, Stubblefield B, Madike V, and Sidransky E (2000) Glucocerebrosidase gene mutations in patients with type 2 Gaucher disease. Hum Mutat, 15:181-8. Sawkar A R, Adamski-Werner S. L., Cheng W.-C., Wong C.-H., Beutler E., Zimmer K.-P. et al. (2005) Gaucher disease-associated glucocerebrosidases show mutation-dependent chemical chaperoning profiles. Chem. Biol. 12: 1235-1244.). Moreover, the first clinical trials for a pharmacological chaperone, isofagomine, were ended due to lack of efficacy for patients with Type I Gaucher disease. There is clearly a critical need to develop new therapies to treat neuronopathic Gaucher disease and pursue alternative strategies to discover effective treatments.

The use of patient derived cells in phenotypic assays has great potential to discover new, breakthrough therapeutics and offers an alternative to target based strategies which have failed to deliver effective treatments (Swinney, D C (2013) The Contribution of Mechanistic Understanding to Phenotypic Screening for First-in-Class Medicines Phenotypic assays in drug discovery. J Biomol Screen. 18:1186-1192.). Availability of LSD patient derived cells provides a unique opportunity to develop phenotypic based screens designed to identify compounds which can either attenuate the underlying pathophysiology or restore function to a normal state to support identification of a new class of disease modifying therapeutics. Recent evidence has proposed that dysfunction of calcium signaling from acidic lysosomal stores is a common pathological feature of LSDs (Lloyd-Evans, E, Morgan A J, He X, Smith D A, Elliot-Smith E, Sillence D J, Churchill G C, Schuchman E H, Galione A, Platt F M. (2008) Niemann-Pick disease type C1 is a sphingosine storage disease that causes deregulation of lysosomal calcium. Nat Med. 14(11): 1247-55. Kilpatrick, B. S.; Magalhaes, J.; Beavan, M. S.; McNeill, A.; Gegg, M. E.; Cleeter, M. E.; Bloor-Youn, D.; Churchill, G. C.; Duchen, M. R.; Schapira, A. H.; Patel, S. Endoplasmic reticulum and lysosomal Ca+2 stores are remodeled in GBA1-Linked Parkinson's disease and patient fibroblasts Ceel Calcium. 2015, Nov. 26, PMID 26691915, Lloyd-Evans E, Platt F M. (2011) Lysosomal Ca(2+) homeostasis: role in pathogenesis of lysosomal storage diseases. Cell Calcium. 50(2):200-205.). Calcium release from acidic stores is required in vesicle membrane fusion and transport in the endosomal/lysosomal system (Morgan, A. J.; Platt, F. M.; Lloyd-Evans, E; Galione, A. (2011) Molecular mechanism of endolysosomal Ca2+ signaling in health and disease. Biochem. J. 439:349-374.). In Niemann-Pick C (NPC) patient derived fibroblasts, a reduction in calcium release from lysosomal acidic stores was detected in response to the lysosmotic agent, Gly-Phe-β-napthylamide (GPN) in comparison with age matched normal patient cells (Lloyd-Evans, E, Morgan A J, He X, Smith D A, Elliot-Smith E, Sillence D J, Churchill G C, Schuchman E H, Galione A, Platt F M. (2008) Niemann-Pick disease type C1 is a sphingosine storage disease that causes deregulation of lysosomal calcium. Nat Med. 14(11):1247-55.). Curcumin, a compound known to increase cytosolic calcium, restored calcium signaling in NPC cells. Furthermore, curcumin treatment improved function and life expectancy in NPC1 disease mouse models ([Lloyd-Evans, E, Morgan A J, He X, Smith D A, Elliot-Smith E, Sillence D J, Churchill G C, Schuchman E H, Galione A, Platt F M. (2008) Niemann-Pick disease type C1 is a sphingosine storage disease that causes deregulation of lysosomal calcium. Nat Med. 14(11): 1247-55.). This study suggested that demonstration of a compound's calcium restorative activity on NPC cells in vitro had potential to predict in vivo efficacy in NPC animal models, and which could lead to the identification of novel therapies for NPC. In principle, the same strategy would apply to other lysosomal storage diseases such as Gaucher disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, GM2 gangliosidosis. To date, however, there are no clinically useful compounds that are capable of preventing or treating lysosomal storage diseases.

Separately, it has been observed that patients with homozygous mutations in the glucocerebrosidase (GBA1) gene have an increased risk of developing Parkinson disease (PD). The GBA1 mutation has been associated with a 20 to 30 fold increase in risk of developing PD. In addition, 7-10% of PD patients have GBA1 mutation. Mutations in the GBA1 gene constitute numerically the most important risk factor for PD (Sidransky and Lopez (2012) Lancet Neurol. 11(11): 986-998; Schapira, A; Migdalska-Richards, A. J. Neurochem. (2016), 10.1111/jnc.13385). PD patients with GBA1 mutations tend to experience an earlier onset of PD when compared to patients without the GBA1 mutation. It has been further suggested that modulation of glucocerebrosidase activity could be a novel approach to the treatment of Parkinson's disease. To date, however, there are no clinically useful treatments for PD that utilize this approach, and the availability of PD therapies is limited. There remains a clear and present need for additional therapies capable of treating and preventing Parkinson's disease. Synucleinopathies such as dementia with Lewy bodies (DLB), pure autonomic failure (PAF), and multiple system atrophy (MSA) are also unmet medical needs that could be addressed in the same manner as described for Parkinson's disease. To date, however, therapies for synucleinopathies such as dementia with Lewy bodies (DLB), pure autonomic failure (PAF), and multiple system atrophy (MSA) are not fully effective. Additional therapies are required.

Separately, fungal infection remains a serious global health issue. Cryptococcosis, for example, affects approximately 1 million people annually and kills more HIV/AIDS patients per year than tuberculosis. The gold standard therapy for cryptococcosis is amphotericin B plus 5-flucytosine, but this regimen is not readily available in regions of the world where resources are limited and where the burden of disease is highest. There is a clear and present need for additional methods and therapies capable of treating fungal infections.

BRIEF SUMMARY OF THE INVENTION

The present invention is directed toward novel functionalized N,N-dialkylamino phenyl ethers, compounds of formula (I),

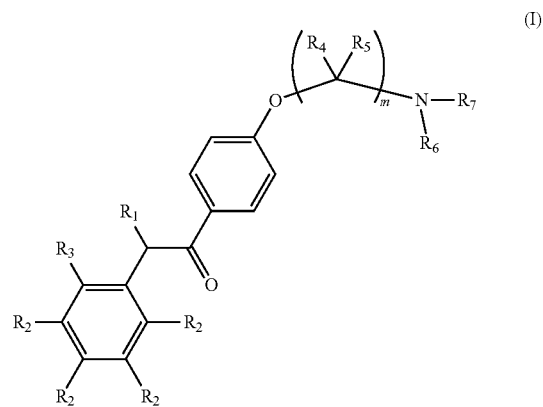

Including enantiomers, diastereomers, hydrates, solvates, pharmaceutically acceptable salts, prodrugs and complexes thereof, wherein:

$R^1$ is selected from the group consisting of hydrogen, $C_1$-$C_6$ linear alkyl, $C_1$-$C_{10}$ branched alkyl, alkenyl, alkynyl, $C_3$-$C_{10}$ cycloalkyl, cycloalkenyl, alkyl-cycloalkyl and alkyl-cycloalkenyl optionally substituted with a $C_1$-$C_5$ alkyl group;

$R^2$ is at each occurrence independently selected from the group consisting of H, OH, halogen, CN, $NO_2$, $C_1$-$C_{10}$ alkoxy, $C_3$-$C_{10}$ branched alkoxy, $C_1$-$C_{10}$ haloalkoxy, $C_3$-$C_{10}$ branched haloalkoxy, $NR^8R^9$, $C(O)OR^{10}$, $C_1$-$C_{10}$ thioalkyl, $C_3$-$C_{10}$ branched thioalkyl, $C_1$-$C_{10}$ halothioalkyl, —$S(O)C_1$-$C_{10}$ alkyl, —$S(O)C_3$-$C_{10}$ branched alkyl, —$S(O)C_1$-$C_{10}$ haloalkyl, —$S(O)C_3$-$C_{10}$ branched haloalkyl, —$SO_2C_1$-$C_{10}$ alkyl, —$SO_2C_3$-$C_{10}$ branched alkyl, —$SO_2C_1$-$C_{10}$ haloalkyl, —$SO_2C_1$-$C_{10}$ branched haloalkyl, $SO_2NR^{11}R^{12}$, —$NR^{11}SO_2R^{13}$, $C(O)$—$NR^{11}R^{12}$;

$R^3$ is a substituted or unsubstituted aryl or heteroaryl group of 1-10 carbon atoms, wherein the heteroaryl group comprises 1-4 heteroatoms, wherein the heteroatom is selected from the group consisting of O, N, S, S(O), $SO_2$, and wherein the aryl or heteroaryl group may be optionally substituted with a substituent selected from the group consisting of H, OH, halogen, CN, $NO_2$, $C_1$-$C_{10}$ alkoxy, $C_3$-$C_{10}$ branched alkoxy, $C_1$-$C_{10}$ haloalkoxy, $C_3$-$C_{10}$ branched haloalkoxy, $NR^8R^9$, $C(O)OR^{10}$, $C_1$-$C_{10}$ thioalkyl, $C_3$-$C_{10}$ branched thioalkyl, $C_1$-$C_{10}$ halothioalkyl, —$S(O)C_1$-$C_1$ alkyl, —$S(O)C_3$-$C_{10}$ branched alkyl, —$S(O)C_1$-$C_{10}$ haloalkyl, —$S(O)C_3$-$C_{10}$ branched haloalkyl, —$SO_2C_1$-$C_{10}$ alkyl, —$SO_2C_3$-$C_{10}$ branched alkyl, —$SO_2C_1$-$C_{10}$ haloalkyl, —$SO_2C_1$-$C_{10}$ branched haloalkyl, $SO_2NR^{11}R^{12}$, —$NR^{11}SO_2R^{13}$, $C(O)$—$NR^{11}R^{12}$;

$R^4$ is at each occurrence independently selected from the group consisting of hydrogen, $C_1$-$C_6$ linear alkyl, and $C_3$-$C_7$ branched alkyl;

$R^5$ is at each occurrence independently selected from the group consisting of hydrogen, $C_1$-$C_6$ linear alkyl, and $C_3$-$C_7$ branched alkyl;

m is 2, 3, 4, 5, 6, 7, 8, 9, or 10;

$R^6$ is selected from the group consisting of hydrogen, $C_1$-$C_6$ linear alkyl and $C_3$-$C_7$ branched alkyl;

$R^7$ is selected from the group consisting of hydrogen, $C_1$-$C_6$ linear alkyl and $C_3$-$C_7$ branched alkyl; or $R^6$ and $R^7$ may optionally be taken together with the atoms to which they are bound to form a ring containing 4 to 7 members, and wherein the ring may optionally comprise a member selected from the group consisting of O, S, and $NR^{14}$;

$R^8$ is at each occurrence independently selected from the group consisting of hydrogen, $C_1$-$C_6$ linear alkyl, and $C_3$-$C_7$ branched alkyl;

$R^9$ is at each occurrence independently selected from the group consisting of hydrogen, $C_1$-$C_6$ linear alkyl, and $C_3$-$C_7$ branched alkyl;

$R^{10}$ is at each occurrence independently selected from the group consisting of hydrogen, $C_1$-$C_6$ linear alkyl, and $C_3$-$C_7$ branched alkyl;

$R^{11}$ is at each occurrence independently selected from the group consisting of hydrogen, $C_1$-$C_6$ linear alkyl, and $C_3$-$C_7$ branched alkyl;

$R^{12}$ is at each occurrence independently selected from the group consisting of hydrogen, $C_1$-$C_6$ linear alkyl, and $C_3$-$C_7$ branched alkyl;

$R^{13}$ is at each occurrence independently selected from the group consisting of hydrogen, $C_1$-$C_6$ linear alkyl, and $C_3$-$C_7$ branched alkyl; and $R^{14}$ is at each occurrence independently selected from the group consisting of hydrogen, $C_1$-$C_6$ linear alkyl, and $C_3$-$C_7$ branched alkyl.

The embodiments of the present invention include compounds having formula (II):

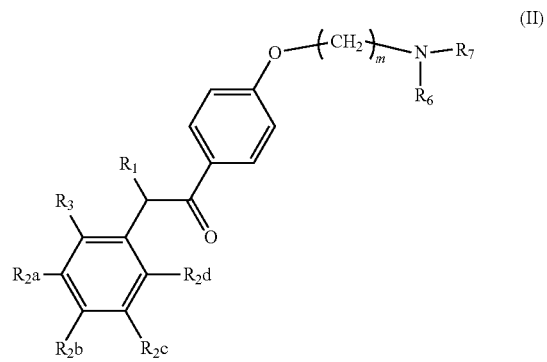

Including enantiomers, diastereomers, hydrates, solvates, enantiomers, diastereomers, pharmaceutically acceptable salts, and complexes thereof.

The embodiments of the present invention include compounds having formula (III):

Including enantiomers, diastereomers, hydrates, solvates, enantiomers, diastereomers, pharmaceutically acceptable salts, and complexes thereof.

The embodiments of the present invention include compounds having formula (V):

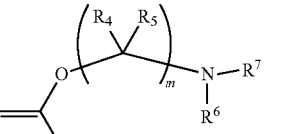

Including enantiomers, diastereomers, hydrates, solvates, enantiomers, diastereomers, pharmaceutically acceptable salts, and complexes thereof.

The present invention further relates to compositions comprising: an effective amount of one or more compounds according to the present invention and an excipient.

The present invention also relates to a method for treating or preventing diseases and conditions that involve lysosomal storage dysfunction, including, for example, Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention.

The present invention yet further relates to a method for treating or preventing diseases and conditions that involve lysosomal storage dysfunction, including, for example, Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, wherein said method comprises administering to a subject a composition comprising an effective amount of one or more compounds according to the present invention and an excipient.

The present invention also relates to a method for treating or preventing disease or conditions associated with Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, and diseases that involve lysosomal storage dysfunction. Said methods comprise administering to a subject an effective amount of a compound or composition according to the present invention.

The present invention yet further relates to a method for treating or preventing disease or conditions associated with Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, and diseases that involve lysosomal storage dysfunction, wherein said method comprises administering to a subject a composition comprising an effective amount of one or more compounds according to the present invention and an excipient.

The present invention also relates to a method for treating or preventing diseases and conditions that involve misfolding of lysosomal related proteins including, for example, Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention.

The present invention also relates to a method for treating or preventing diseases and conditions that involve misfolding of lysosomal related proteins including, for example, Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention and an excipient.

The present invention yet further relates to a method for treating or preventing disease or conditions associated with Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, and diseases that involve misfolding of lysosomal related proteins, wherein said method comprises administering to a subject a composition comprising an effective amount of one or more compounds according to the present invention and an excipient.

The present invention also relates to a method for treating or preventing diseases and conditions that involve misfolding of lysosomal related proteins including, for example, Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, said method comprising administering to a subject an effective amount of a compound or composition according to the present invention.

The present invention also relates to a method for treating or preventing Parkinson's disease. Said methods comprise administering to a subject an effective amount of a compound or composition according to the present invention.

The present invention also relates to a method for treating or preventing Parkinson's disease, wherein said methods comprise administering to a subject an effective amount of a compound or composition according to the present invention and an excipient.

The present invention also relates to a method for treating or preventing synucleinopathies such as dementia with Lewy bodies (DLB), pure autonomic failure (PAF), and multiple system atrophy (MSA). Said methods comprise administering to a subject an effective amount of a compound or composition according to the present invention.

The present invention also relates to a method for treating or preventing synucleinopathies such as dementia with Lewy bodies (DLB), pure autonomic failure (PAF), and multiple system atrophy (MSA), wherein said methods comprise administering to a subject an effective amount of a compound or composition according to the present invention and an excipient.

The present invention also relates to a method for treating or preventing disease or conditions associated with calcium signaling dysfunction. Said methods comprise administering to a subject an effective amount of a compound or composition according to the present invention.

The present invention yet further relates to a method for treating or preventing disease or conditions associated with calcium signaling dysfunction, wherein said method comprises administering to a subject a composition comprising an effective amount of one or more compounds according to the present invention and an excipient.

The present invention also relates to a method for treating or preventing disease or conditions associated with β-glucocerebrosidase dysfunction. Said methods comprise administering to a subject an effective amount of a compound or composition according to the present invention.

The present invention yet further relates to a method for treating or preventing disease or conditions associated with β-glucocerebrosidase dysfunction, wherein said method comprises administering to a subject a composition comprising an effective amount of one or more compounds according to the present invention and an excipient.

The present invention also relates to a method for treating or preventing disease or conditions associated with α-galactosidase A dysfunction. Said methods comprise administering to a subject an effective amount of a compound or composition according to the present invention.

The present invention yet further relates to a method for treating or preventing disease or conditions associated with α-galactosidase A dysfunction, wherein said method comprises administering to a subject a composition comprising an effective amount of one or more compounds according to the present invention and an excipient.

The present invention also relates to a method for treating or preventing disease or conditions associated with β-galactosidase dysfunction. Said methods comprise administering to a subject an effective amount of a compound or composition according to the present invention.

The present invention yet further relates to a method for treating or preventing disease or conditions associated with β-galactosidase dysfunction, wherein said method comprises administering to a subject a composition comprising an effective amount of one or more compounds according to the present invention and an excipient.

The present invention also relates to a method for treating or preventing disease or conditions associated with β-hexosaminidase dysfunction. Said methods comprise administering to a subject an effective amount of a compound or composition according to the present invention.

The present invention yet further relates to a method for treating or preventing disease or conditions associated with β-hexosaminidase dysfunction, wherein said method comprises administering to a subject a composition comprising an effective amount of one or more compounds according to the present invention and an excipient.

The present invention also relates to a method for treating or preventing disease or conditions associated with α-glucosidase dysfunction. Said methods comprise administering to a subject an effective amount of a compound or composition according to the present invention.

The present invention yet further relates to a method for treating or preventing disease or conditions associated with α-glucosidase dysfunction, wherein said method comprises administering to a subject a composition comprising an effective amount of one or more compounds according to the present invention and an excipient.

The present invention also relates to a method for treating or preventing disease or conditions associated with N-acetylgalactosamine-4-sulfatase dysfunction. Said methods comprise administering to a subject an effective amount of a compound or composition according to the present invention.

The present invention yet further relates to a method for treating or preventing disease or conditions associated with N-acetylgalactosamine-4-sulfatase dysfunction, wherein said method comprises administering to a subject a composition comprising an effective amount of one or more compounds according to the present invention and an excipient.

The present invention also relates to a method for treating or preventing disease or conditions associated with heparan sulfate acetyl-CoA dysfunction. Said methods comprise administering to a subject an effective amount of a compound or composition according to the present invention.

The present invention yet further relates to a method for treating or preventing disease or conditions associated with heparan sulfate acetyl-CoA dysfunction, wherein said method comprises administering to a subject a composition comprising an effective amount of one or more compounds according to the present invention and an excipient.

The present invention also relates to a method for treating or preventing disease or conditions associated with α-glucosaminidine N-acetyltransferase dysfunction. Said methods comprise administering to a subject an effective amount of a compound or composition according to the present invention.

The present invention yet further relates to a method for treating or preventing disease or conditions associated with α-glucosaminidine N-acetyltransferase dysfunction, wherein said method comprises administering to a subject a composition comprising an effective amount of one or more compounds according to the present invention and an excipient.

The present invention also relates to a method for treating or preventing disease or conditions associated with N-acetylgalactosamine-4-sulfatase dysfunction. Said methods comprise administering to a subject an effective amount of a compound or composition according to the present invention.

The present invention yet further relates to a method for treating or preventing disease or conditions associated with N-acetylgalactosamine-4-sulfatase dysfunction, wherein said method comprises administering to a subject a composition comprising an effective amount of one or more compounds according to the present invention and an excipient.

The present invention also relates to a method for treating or preventing disease or conditions associated with galactocerebrosidase dysfunction. Said methods comprise administering to a subject an effective amount of a compound or composition according to the present invention.

The present invention yet further relates to a method for treating or preventing disease or conditions associated with galactocerebrosidase dysfunction, wherein said method comprises administering to a subject a composition comprising an effective amount of one or more compounds according to the present invention and an excipient.

The present invention also relates to a method for treating or preventing disease or conditions associated with mucolipins 1 (TRPML1) dysfunction. Said methods comprise administering to a subject an effective amount of a compound or composition according to the present invention.

The present invention yet further relates to a method for treating or preventing disease or conditions associated with mucolipins 1 (TRPML1) dysfunction, wherein said method comprises administering to a subject a composition comprising an effective amount of one or more compounds according to the present invention and an excipient.

The present invention also relates to a method for treating or preventing disease or conditions associated with mucolipins 2 (TRPML2) dysfunction. Said methods comprise administering to a subject an effective amount of a compound or composition according to the present invention.

The present invention yet further relates to a method for treating or preventing disease or conditions associated with mucolipins 2 (TRPML2) dysfunction, wherein said method comprises administering to a subject a composition comprising an effective amount of one or more compounds according to the present invention and an excipient.

The present invention also relates to a method for treating or preventing disease or conditions associated with mucolipins 3 (TRPML3) dysfunction. Said methods comprise administering to a subject an effective amount of a compound or composition according to the present invention.

The present invention yet further relates to a method for treating or preventing disease or conditions associated with mucolipins 3 (TRPML3) dysfunction, wherein said method comprises administering to a subject a composition comprising an effective amount of one or more compounds according to the present invention and an excipient.

The present invention yet further relates to a method for treating or preventing fungal infections. Said methods comprise administering to a subject an effective amount of a compound or composition according to the present invention.

The present invention yet further relates to a method for treating or preventing fungal infections wherein said method comprises administering to a subject a composition comprising an effective amount of one or more compounds according to the present invention and an excipient.

The present invention further relates to a process for preparing the functionalized N,N-dialkylamino phenyl ethers of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF THE DRAWINGS

FIGS. 7A-7E, depicts confocal images of MDW933 labeling. FIG. 7A depicts confocal images of MDW933 labeling in WT. FIG. 7B depicts confocal images of MDW933 labeling in GD L444P fibroblasts. FIG. 7C depicts confocal images of MDW933 labeling in GD L444P treated with HTS hit. GCase specific MDW933 (green) and DAPI (blue), Magnification 63×, scale bar=50 μm FIG. 7D is a graph of experimental data demonstrating the mean fluorescence intensity for MDW933 labeling. Fluorescence intensity was measured from 30 cells per field, n=3. Solid bar, WT, open bar GD L444P/L444P, gray bar L444P/L444P treated with 5 μM MC290045. * $p<0.0001$ GD L444P vs WT and  $p<0.05$ GD L444P with MC290045 treatment vs vehicle treated GD L444P was assessed by Student's t-test. FIG. 7E depicts the structure of compound MC-290045.

DETAILED DESCRIPTION OF THE INVENTION

The functionalized N,N-dialkylamino phenyl ethers of the present invention and composition thereof are capable of treating and preventing diseases and conditions that involve lysosomal storage dysfunction, for example Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis. Further, it has been discovered that the compounds of the disclosure and compositions thereof are useful for treating or preventing disease or conditions associated with Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis, and diseases that involve lysosomal storage dysfunction. The compounds of the disclosure and compositions thereof are also capable of treating or preventing diseases and conditions that involve misfolding of lysosomal related proteins. The compounds of the disclosure and compositions thereof are also capable of treating or preventing diseases and conditions that are associated with misfolding of lysosomal related proteins. The compounds of the disclosure and compositions thereof are also capable of treating or preventing diseases and conditions that involve calcium signaling dysfunction. The compounds of the disclosure and compositions thereof are also capable of treating or preventing diseases and conditions that are associated with calcium signaling dysfunction.

In one embodiment, the disease is Type 1 Gaucher's disease.

In one embodiment, the disease is Type 2 Gaucher's disease.

In one embodiment, the disease is Type 3 Gaucher's disease.

Figure 1:
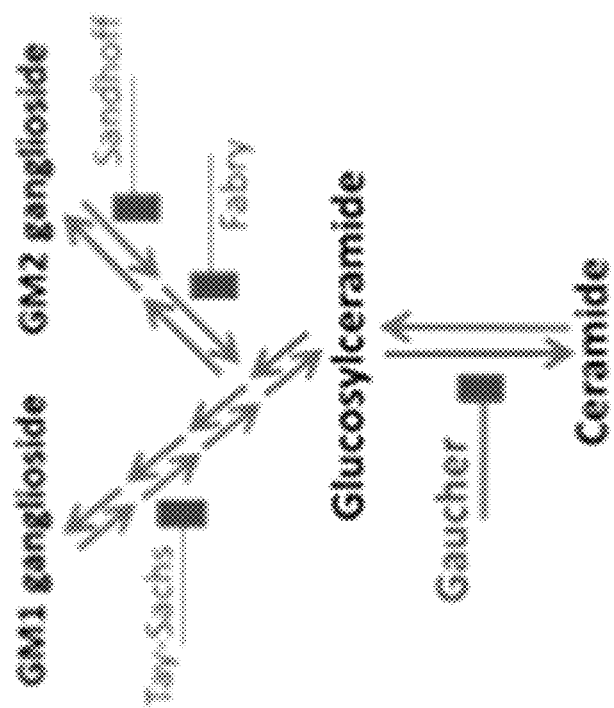
FIG. 1 is a flow chart depicting how Lysosomal Storage Diseases (LSDs) are caused by deficiencies in glycosphingolipid degradative enzymes.
Figure 2:
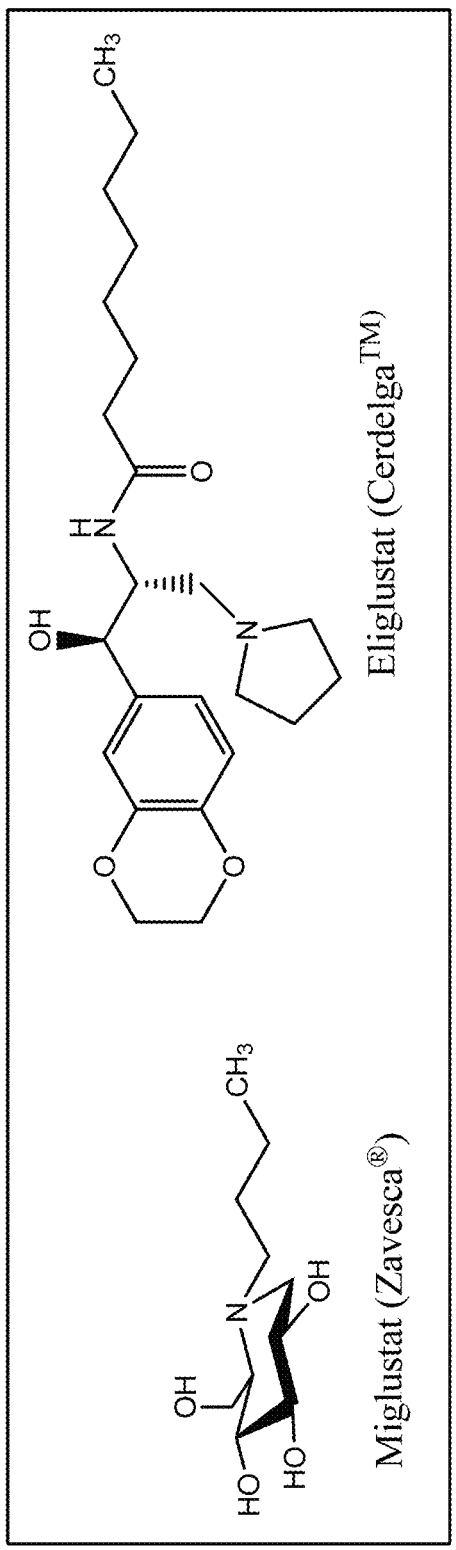
FIG. 2 depicts the structures of marketed glucosylceramide synthase inhibitors for Type 1 Gaucher.

Compounds of the present invention are useful for restoring a normal phenotype to diseased patient cells, and are able to penetrate the CNS and thus exhibit improved properties over known treatment for Gaucher's disease such as enzyme replacement therapy (ERT) and glucosylceramide synthase inhibitors. ERT can only be used to treat Type 1 Gaucher's disease, which is limited to peripheral tissues. It cannot be used to treat CNS-associated Type-2 and Type-3 Gaucher's disease. Glucosylceramide synthase inhibitors, such as eliglustat (Cerdelga™) and Miglustat (Zavesca®) (FIG. 2), are marketed for the treatment of Type 1 Gaucher's disease but because of their extreme polarity, these compounds do not enter the CNS and cannot be used to treat the CNS-associated forms of the disease. In contrast, the compounds of the present invention are non-polar small molecules that can penetrate into the CNS and thus provide a viable treatment option for neuronopathic Gaucher disease.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

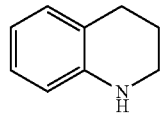

is, for the purposes of the present invention, considered a heterocyclic unit. 6,7-Dihydro-5H-cyclopentapyrimidine having the formula:

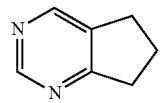

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

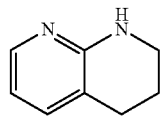

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I), —CN, —NO$_2$, oxo (=O), —OR$^{15}$, —SR$^{15}$, —N(R$^{15}$)$_2$, —NR$^{15}$C(O)R$^{15}$, —SO$_2$R$^{15}$, —SO$_2$OR$^{15}$, —SO$_2$N(R$^{15}$)$_2$, —C(O)R$^{15}$, —C(O)OR$^{15}$, —C(O)N(R$^{15}$)$_2$, $C_{1-6}$ alkyl, $C_{1-6}$ haloalkyl, $C_{1-6}$alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{15}$; wherein R$^{15}$, at each occurrence, independently is hydrogen, —OR$^{16}$, —SR$^{16}$, —C(O)R$^{16}$, —C(O)OR$^{16}$, —C(O)N(R$^{16}$)$_2$, —SO$_2$R$^{16}$, —S(O)$_2$OR$^{16}$, —N(R$^{16}$)$_2$, —NR$^{16}$C(O)R$^{16}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{15}$ units taken together with the atom(s) to which they are bound form an optionally substituted carbocycle or heterocycle wherein said carbocycle or heterocycle has 3 to 7 ring atoms; wherein R$^{16}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{15}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{17}$; for example, —OH, —OCH$_3$, —OCH$_2$CH$_3$, —OCH$_2$CH$_2$CH$_3$;
ii) —C(O)R$^{17}$; for example, —COCH$_3$, —COCH$_2$CH$_3$, —COCH$_2$CH$_2$CH$_3$;
iii) —C(O)OR$^{17}$; for example, —CO$_2$CH$_3$, —CO$_2$CH$_2$CH$_3$, —CO$_2$CH$_2$CH$_2$CH$_3$;
iv) —C(O)N(R$^{17}$)$_2$; for example, —CONH$_2$, —CONHCH$_3$, —CON(CH$_3$)$_2$;
v) —N(R$^{17}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{17}$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^{17}$)C(O)R$^{17}$;
xiii) Oxo (=O);
xiv) Heterocycle; and
xv) Heteroaryl.

wherein each R$^{17}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two R$^{17}$ units can be taken together to form a ring comprising 3-7 ring atoms. In certain aspects, each R$^{17}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$—C, and $C_5$-$C_6$, alkyl.

For the purposes of the present invention the terms "compound," "analog," and "composition of matter" stand equally well for the functionalized N,N-dialkylamino phenyl ethers described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{16})_2$, each $R^{16}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Functionalized N,N-Dialkylamino Phenyl Ethers

The compounds of the present invention include functionalized N,N-dialkylamino phenyl ethers, and include all enantiomeric and diastereomeric forms and pharmaceutically accepted salts thereof having the formula:

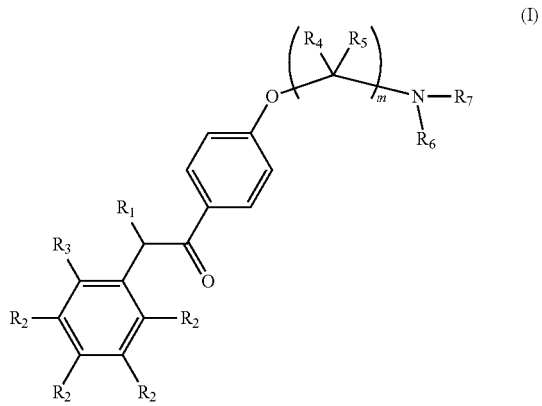

(I)

Including enantiomers, diastereomers, hydrates, solvates, pharmaceutically acceptable salts, prodrugs and complexes thereof, wherein:

$R^1$ is selected from the group consisting of hydrogen, $C_1$-$C_6$ linear alkyl, $C_1$-$C_{10}$ branched alkyl, alkenyl, alkynyl, $C_3$-$C_{10}$ cycloalkyl, cycloalkenyl, alkyl-cycloalkyl and alkyl-cycloalkenyl optionally substituted with a $C_1$-$C_5$ alkyl group;

$R^2$ is at each occurrence independently selected from the group consisting of H, OH, halogen, CN, $NO_2$, $C_1$-$C_{10}$ alkoxy, $C_3$-$C_{10}$ branched alkoxy, $C_1$-$C_{10}$ haloalkoxy, $C_3$-$C_{10}$ branched haloalkoxy, $NR^8R^9$, $C(O)OR^{10}$, $C_1$-$C_{10}$ thioalkyl, $C_3$-$C_{10}$ branched thioalkyl, $C_1$-$C_{10}$ halothioalkyl, —S(O)$C_1$-$C_{10}$ alkyl, —S(O)$C_3$-$C_{10}$ branched alkyl, —S(O)$C_1$-$C_{10}$ haloalkyl, —S(O)$C_3$-$C_{10}$ branched haloalkyl, —SO$_2$$C_1$-$C_{10}$ alkyl, —SO$_2$$C_3$-$C_{10}$ branched alkyl, —SO$_2$$C_1$-$C_{10}$ haloalkyl, —SO$_2$$C_1$-$C_{10}$ branched haloalkyl, $SO_2NR^{11}R^{12}$, —$NR^{11}SO_2R^{13}$, $C(O)$—$NR^{11}R^{12}$;

$R^3$ is a substituted or unsubstituted aryl or heteroaryl group of 1-10 carbon atoms, wherein the heteroaryl group comprises 1-4 heteroatoms, wherein the heteroatom is selected from the group consisting of O, N, S, S(O), $SO_2$, and wherein the aryl or heteroaryl group may be optionally substituted with a substituent selected from the group consisting of H, OH, halogen, CN, $NO_2$, $C_1$-$C_{10}$ alkoxy, $C_3$-$C_{10}$ branched alkoxy, $C_1$-$C_{10}$ haloalkoxy, $C_3$-$C_{10}$ branched haloalkoxy, $NR^8R^9$, $C(O)OR^{10}$, $C_1$-$C_{10}$ thioalkyl, $C_3$-$C_{10}$ branched thioalkyl, $C_1$-$C_{10}$ halothioalkyl, —S(O)$C_1$-$C_{10}$ alkyl, —S(O)$C_3$-$C_{10}$ branched alkyl, —S(O)$C_1$-$C_{10}$ haloalkyl, —S(O)$C_3$-$C_{10}$ branched haloalkyl, —SO$_2$$C_1$-$C_{10}$ alkyl, —SO$_2$$C_3$-$C_{10}$ branched alkyl, —SO$_2$$C_1$-$C_{10}$ haloalkyl, —SO$_2$$C_1$-$C_{10}$ branched haloalkyl, $SO_2NR^{11}R^{12}$, —$NR^{11}SO_2R^{13}$, $C(O)$—$NR^{11}R^{12}$;

$R^4$ is at each occurrence independently selected from the group consisting of hydrogen, $C_1$-$C_6$ linear alkyl, and $C_3$-$C_7$ branched alkyl;

$R^5$ is at each occurrence independently selected from the group consisting of hydrogen, $C_1$-$C_6$ linear alkyl, and $C_3$-$C_7$ branched alkyl;

m is 2, 3, 4, 5, 6, 7, 8, 9, or 10;

$R^6$ is selected from the group consisting of hydrogen, $C_1$-$C_6$ linear alkyl and $C_3$-$C_7$ branched alkyl;

$R^7$ is selected from the group consisting of hydrogen, $C_1$-$C_6$ linear alkyl and $C_3$-$C_7$ branched alkyl; or $R^6$ and $R^7$ may optionally be taken together with the atoms to which they are bound to form a ring containing 4 to 7 members, and wherein the ring may optionally comprise a member selected from the group consisting of O, S, and $NR^4$;

$R^8$ is at each occurrence independently selected from the group consisting of hydrogen, $C_1$-$C_6$ linear alkyl, and $C_3$-$C_7$ branched alkyl;

$R^9$ is at each occurrence independently selected from the group consisting of hydrogen, $C_1$-$C_6$ linear alkyl, and $C_3$-$C_7$ branched alkyl;

$R^{10}$ is at each occurrence independently selected from the group consisting of hydrogen, $C_1$-$C_6$ linear alkyl, and $C_3$-$C_7$ branched alkyl;

$R^{11}$ is at each occurrence independently selected from the group consisting of hydrogen, $C_1$-$C_6$ linear alkyl, and $C_3$-$C_7$ branched alkyl;

$R^{12}$ is at each occurrence independently selected from the group consisting of hydrogen, $C_1$-$C_6$ linear alkyl, and $C_3$-$C_7$ branched alkyl;

$R^{13}$ is at each occurrence independently selected from the group consisting of hydrogen, $C_1$-$C_6$ linear alkyl, and $C_3$-$C_7$ branched alkyl; and $R^{14}$ is at each occurrence independently selected from the group consisting of hydrogen, $C_1$-$C_6$ linear alkyl, and $C_3$-$C_7$ branched alkyl.

The embodiments of the present invention include compounds having formula (II):

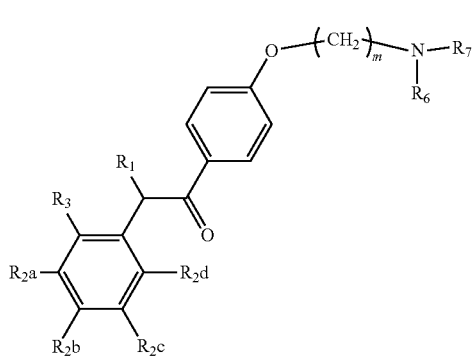

(II)

Including enantiomers, diastereomers, hydrates, solvates, enantiomers, diastereomers, pharmaceutically acceptable salts, and complexes thereof.

The embodiments of the present invention include compounds having formula (III):

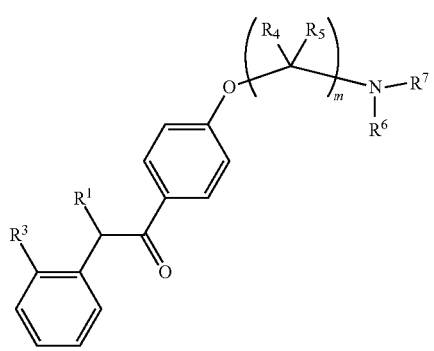

(III)

Including enantiomers, diastereomers, hydrates, solvates, enantiomers, diastereomers, pharmaceutically acceptable salts, and complexes thereof.

The embodiments of the present invention include compounds having formula (V):

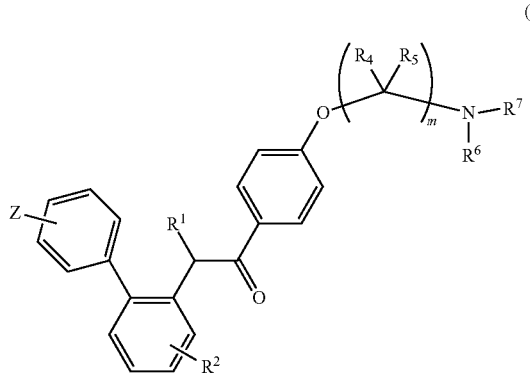

(IV)

Including enantiomers, diastereomers, hydrates, solvates, enantiomers, diastereomers, pharmaceutically acceptable salts, and complexes thereof.

In some embodiments $R^1$ is hydrogen.
In some embodiments $R^1$ is $C_{1-6}$ linear alkyl.
In some embodiments $R^1$ is $C_{3-10}$ branched alkyl.
In some embodiments $R^1$ is alkenyl.
In some embodiments $R^1$ is alkynyl.
In some embodiments $R^1$ is $C_{3-10}$ cycloalkyl.
In some embodiments $R^1$ is cycloalkenyl.
In some embodiments $R^1$ is alkyl-cycloalkyl.
In some embodiments $R^1$ is alkyl-cycloalkenyl.
In some embodiments $R^2$ is H.
In some embodiments $R^2$ is OH.
In some embodiments $R^2$ is halogen.
In some embodiments $R^2$ is CN.
In some embodiments $R^2$ is $NO_2$.
In some embodiments $R^2$ is $C_{1-10}$ alkoxy.
In some embodiments $R^2$ is $C_{3-10}$ branched alkoxy.
In some embodiments $R^2$ is $C_{1-10}$ haloalkoxy.
In some embodiments $R^2$ is $C_{3-10}$ branched haloalkoxy.
In some embodiments $R^2$ is $NR^8R^9$.
In some embodiments $R^2$ is $C(O)OR^{10}$.
In some embodiments $R^2$ is $C_{1-10}$ thioalkyl.
In some embodiments $R^2$ is $C_{3-10}$ branched thioalkyl.
In some embodiments $R^2$ is $C_{1-10}$ halothioalkyl.
In some embodiments $R^2$ is $-S(O)C_{1-10}$ alkyl.
In some embodiments $R^2$ is $-S(O)C_{3-10}$ branched alkyl.
In some embodiments $R^2$ is $-S(O)C_{1-10}$ haloalkyl.
In some embodiments $R^2$ is $-S(O)C_{3-10}$ branched haloalkyl.
In some embodiments $R^2$ is $-SO_2C_{1-10}$ alkyl.
In some embodiments $R^2$ is $-SO_2C_{3-10}$ branched alkyl.
In some embodiments $R^2$ is $-SO_2C_{1-10}$ haloalkyl.
In some embodiments $R^2$ is $-SO_2C_{3-10}$ branched haloalkyl.
In some embodiments $R^2$ is $SO_2NR^{11}R^{12}$.
In some embodiments $R^2$ is $-NR^{11}SO_2R^{13}$.
In some embodiments $R^2$ is $C(O)-NR^{11}R^{12}$.
In some embodiments $R^3$ is a substituted aryl.
In some embodiments $R^3$ is an unsubstituted aryl.
In some embodiments $R^3$ is a substituted heteroaryl.
In some embodiments $R^3$ is an unsubstituted heteroaryl.
In some embodiments $R^4$ is hydrogen.
In some embodiments $R^4$ is $C_{1-6}$ linear alkyl.
In some embodiments $R^4$ is $C_3$-7 branched alkyl.
In some embodiments $R^5$ is hydrogen.
In some embodiments $R^5$ is $C_{1-6}$ linear alkyl.
In some embodiments $R^5$ is $C_3$-7 branched alkyl.
In some embodiments $R^6$ is $C_{1-6}$ linear alkyl.
In some embodiments $R^6$ is $C_3$-7 branched alkyl.
In some embodiments $R^6$ is hydrogen.
In some embodiments $R^7$ is $C_{1-6}$ linear alkyl.
In some embodiments $R^7$ is $C_3$-7 branched alkyl.
In some embodiments $R^7$ is hydrogen.
In some embodiments $R^2a$, $R^2b$, $R^2c$, and $R^2d$ have the same definitions as $R^2$.
In some embodiments at least one of $R^6$ and $R^7$ is selected from the group consisting of $C_1$-$C_6$ linear alkyl and $C_3$-$C_7$ branched alkyl.
In some embodiments $R^6$ and $R^7$ are taken together with the atoms to which they are bound to form a ring containing 4 members, and wherein the ring may optionally comprise a member selected from the group consisting of O, S, and $NR^{14}$.
In some embodiments $R^6$ and $R^7$ are taken together with the atoms to which they are bound to form a ring containing 5 members, and wherein the ring may optionally comprise a member selected from the group consisting of O, S, and $NR^{14}$.

In some embodiments R⁶ and R⁷ are taken together with the atoms to which they are bound to form a ring containing 6 members, and wherein the ring may optionally comprise a member selected from the group consisting of O, S, and NR¹⁴.

In some embodiments R⁶ and R⁷ are taken together with the atoms to which they are bound to form a ring containing 7 members, and wherein the ring may optionally comprise a member selected from the group consisting of O, S, and NR¹⁴.

In some embodiments at least one of R⁶ and R⁷ is selected from the group consisting of $C_1$-$C_6$ linear alkyl and $C_3$-$C_7$ branched alkyl; or R⁶ and R⁷ may optionally be taken together with the atoms to which they are bound to form a ring containing 4 to 7 members, and wherein the ring may optionally comprise a member selected from the group consisting of O, S, and NR¹⁴.

In some embodiments R⁸ is hydrogen.
In some embodiments R⁸ is $C_{1-6}$ linear alkyl.
In some embodiments R⁸ is $C_{3-7}$ branched alkyl.
In some embodiments R⁹ is hydrogen.
In some embodiments R⁹ is $C_{1-6}$ linear alkyl.
In some embodiments R⁹ is $C_{3-7}$ branched alkyl.
In some embodiments R¹⁰ is hydrogen.
In some embodiments R¹⁰ is $C_{1-6}$ linear alkyl.
In some embodiments R¹⁰ is $C_{3-7}$ branched alkyl.
In some embodiments R¹¹ is hydrogen.
In some embodiments R¹¹ is $C_{1-6}$ linear alkyl.
In some embodiments R¹¹ is $C_{3-7}$ branched alkyl.
In some embodiments R¹² is hydrogen.
In some embodiments R¹² is $C_{1-6}$ linear alkyl.
In some embodiments R¹² is $C_{3-7}$ branched alkyl.
In some embodiments R¹³ is hydrogen.
In some embodiments R¹³ is $C_{1-6}$ linear alkyl.
In some embodiments R¹³ is $C_{3-7}$ branched alkyl.
In some embodiments R¹⁴ is hydrogen.
In some embodiments R¹⁴ is $C_{1-6}$ linear alkyl.
In some embodiments R¹⁴ is $C_{3-7}$ branched alkyl.
In some embodiments m is 2.
In some embodiments m is 3.
In some embodiments m is 4.
In some embodiments m is 5.
In some embodiments m is 6.
In some embodiments m is 7.
In some embodiments m is 8.
In some embodiments m is 9.
In some embodiments m is 10.

Non-limiting examples of compounds of the present invention include:

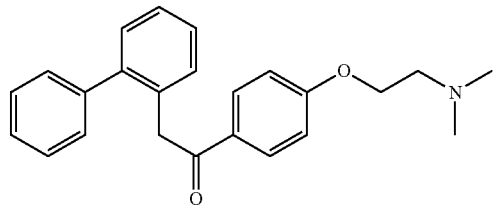 [SMILES: CN(C)CCOc1ccc(C(=O)Cc2ccccc2-c2ccccc2)cc1]

2-([1,1'-Biphenyl]-2-yl)-1-(4-(dimethylamino)-ethoxy)phenyl)ethanone (MC-290041)

-continued

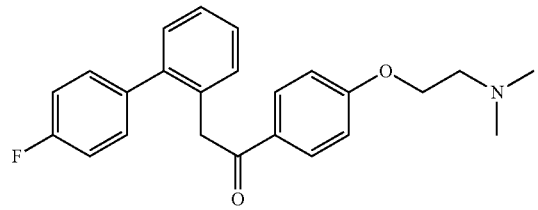

1-(4-(2-(Dimethylamino)ethoxy)phenyl)-2-(4'-fluoro-[1,1'-biphenyl]-2-yl)ethanone (MC-290042)

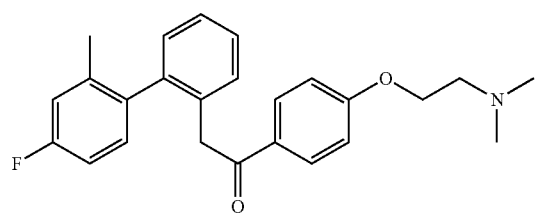

1-(4-(2-(Dimethylamino)ethoxy)phenyl)-2-(4'-fluoro-2'-methyl-[1,1'-biphenyl]-2-yl)ethanone (MC-290059)

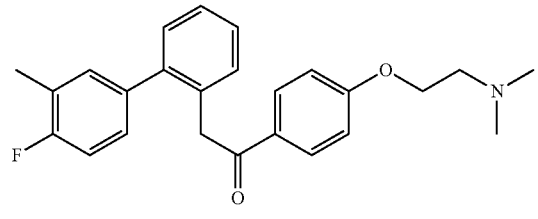

1-(4-(2-(Dimethylamino)ethoxy)phenyl)-2-(4'-fluoro-3'-methyl-[1,1'-biphenyl]-2-yl)ethanone (MC-290060)

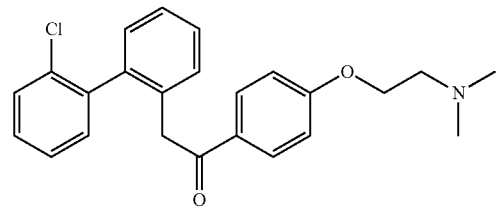

2-(2'-Chloro-[1,1'-biphenyl]-2-yl)-1-(4-(2-(dimethylamino)ethoxy)phenyl)ethanone (MC-290063)

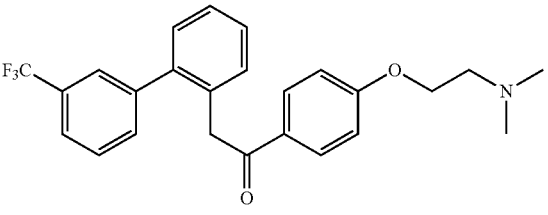

1-(4-(2-(Dimethylamino)ethoxy)phenyl)-2-(3'-(trifluoromethyl)-[1,1'-biphenyl]-2-yl)ethanone (MC-290063)

-continued

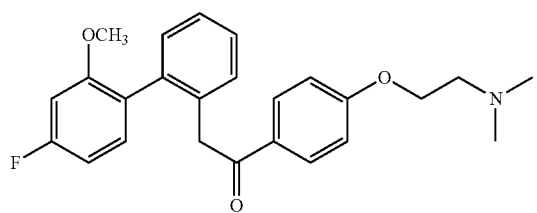

1-(4-(2-(Dimethylamino)ethoxy)phenyl)-2-
(4′-fluoro-2′-methoxy-[1,1′-biphenyl]-2-
yl)ethanone (MC-290064)

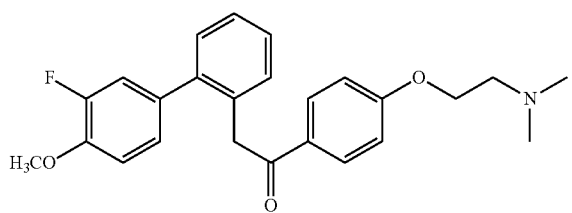

1-(4-(2-(Dimethylamino)ethoxy)phenyl)-2-(3′-
fluoro-4′-methoxy-[1,1′-biphenyl]-2-yl)ethanone
(MC-290065)

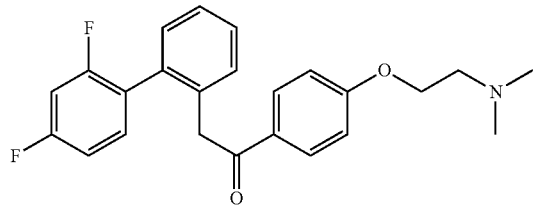

2-(2′,4′-Difluoro-[1,1′-biphenyl]-2-yl)-1-(4-(2-
((dimethylamino)ethoxy)phenyl)ethanone
(MC-290066)

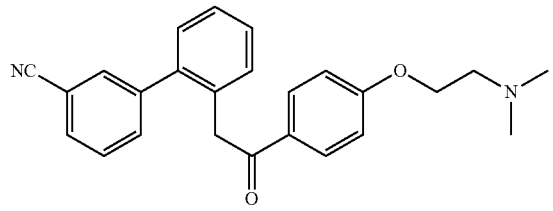

1-(4-(2-(Dimethylamino)ethoxy)phenyl)-2-(3′-
cyano-[1,1′-biphenyl]-2-yl)ethanone
(MC-290067)

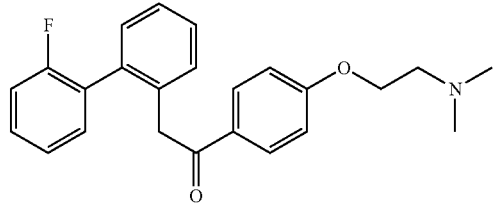

1-(4-(2-(Dimethylamino)ethoxy)phenyl)-2-
(2′-fluoro-[1,1′-biphenyl]-2-yl)ethanone
(MC-290068)

-continued

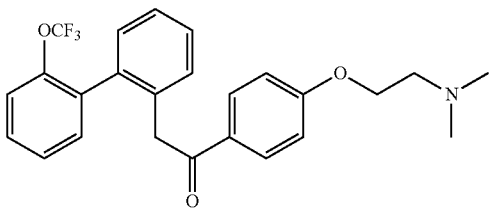

1-(4-(2-(Dimethylamino)ethoxy)phenyl)-2-(2′-
(trifluoromethoxy-[1,1′-biphenyl]-2-yl)ethanone
(MC-290069)

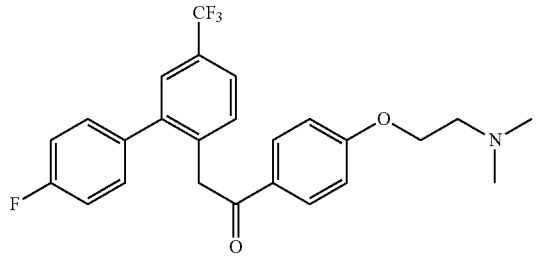

1-(4-(2-(Dimethylamino)ethoxy)phenyl)-2-
(4′-fluoro-5-(trifluoromethyl)-[1,1′-biphenyl]-
2-yl)ethanone (MC-290070)

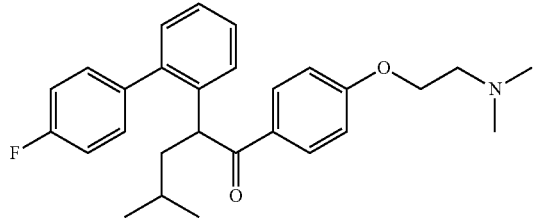 [SMILES: CC(C)CC(C(=O)c1ccc(OCCN(C)C)cc1)c1ccccc1-c1ccc(F)cc1]

1-(4-(2-(Dimethylamino(ethoxy)phenyl)-2-(4′-
fluoro-[1,1′-biphenyl]-2-yl)-4-methylpentan-1-
one (MC 290284)

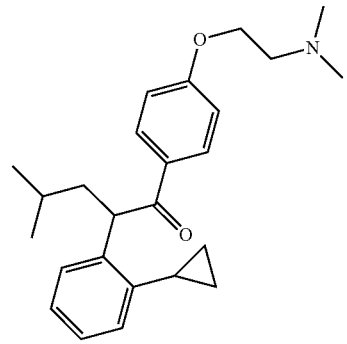

2-(2-cyclopropylphenyl)-1-(4-(2-
(dimethylamino)ethoxy)phenyl)-4-
methylpentan-1-one (MC-290045)

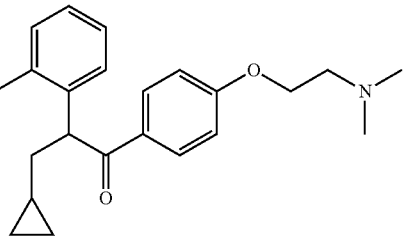

3-cyclopropyl-1-(4-(2-
(dimethylamino)ethoxy)phenyl)-2-(4′-fluoro-[1,1′-
biphenyl]-2-yl)propan-1-one (MC 290295)

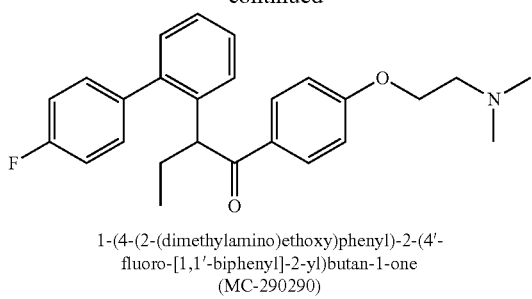

1-(4-(2-(dimethylamino)ethoxy)phenyl)-2-(4'-fluoro-[1,1'-biphenyl]-2-yl)butan-1-one (MC-290290)

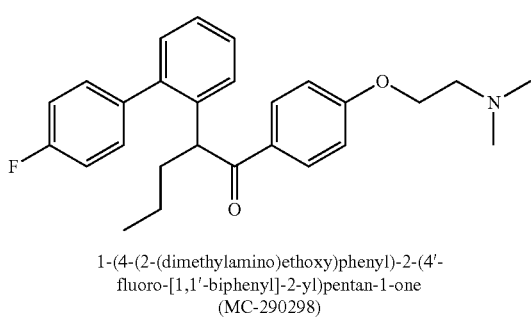

1-(4-(2-(dimethylamino)ethoxy)phenyl)-2-(4'-fluoro-[1,1'-biphenyl]-2-yl)pentan-1-one (MC-290298)

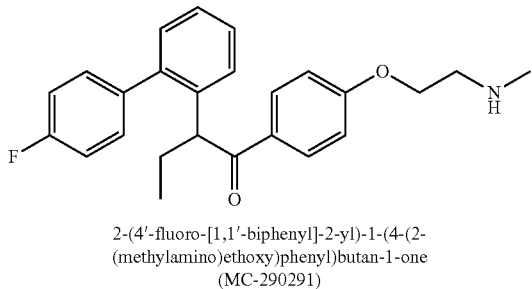

2-(4'-fluoro-[1,1'-biphenyl]-2-yl)-1-(4-(2-(methylamino)ethoxy)phenyl)butan-1-one (MC-290291)

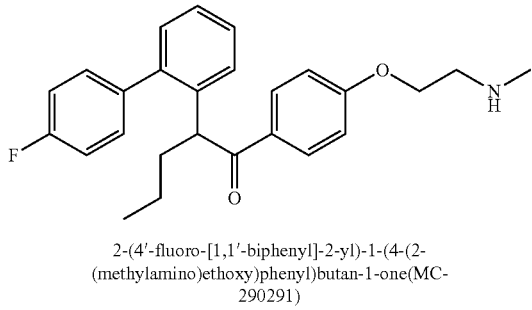

2-(4'-fluoro-[1,1'-biphenyl]-2-yl)-1-(4-(2-(methylamino)ethoxy)phenyl)butan-1-one(MC-290291)

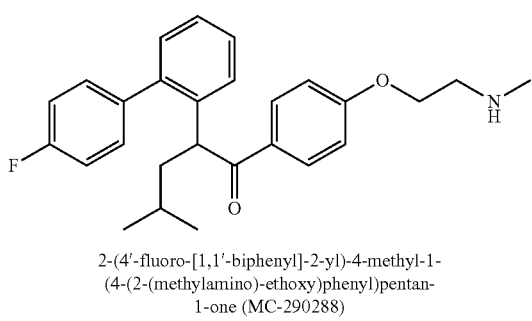

2-(4'-fluoro-[1,1'-biphenyl]-2-yl)-4-methyl-1-(4-(2-(methylamino)-ethoxy)phenyl)pentan-1-one (MC-290288)

For the purposes of demonstrating the manner in which the compounds of the present invention are named and referred to herein, the compound having the formula:

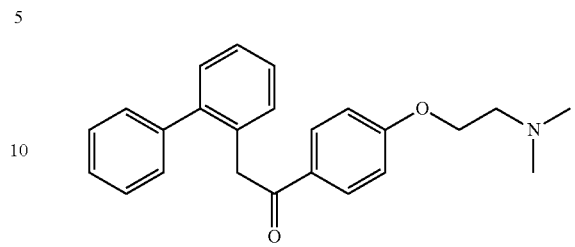

has the chemical name 2-([1,1'-biphenyl]-2-yl)-1-(4-(dimethylamino)-ethoxy)phenyl)ethanone.

For the purposes of demonstrating the manner in which the compounds of the present invention are named and referred to herein, the compound having the formula:

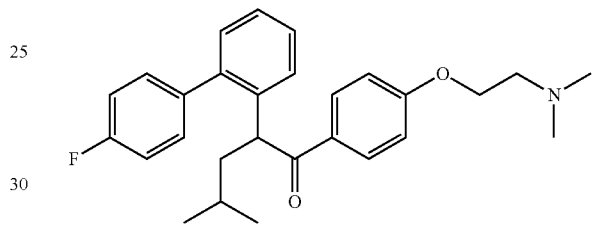

has the chemical name 1-(4-(2-(dimethylamino)ethoxy)phenyl)-2-(4'-fluoro-[1,1'-biphenyl]-2-yl)-4-methylpentan-1-one.

For the purposes of the present invention, a compound depicted by the racemic formula, for example:

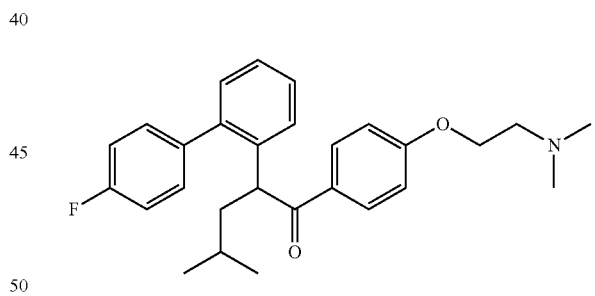

will stand equally well for either of the two enantiomers having the formula:

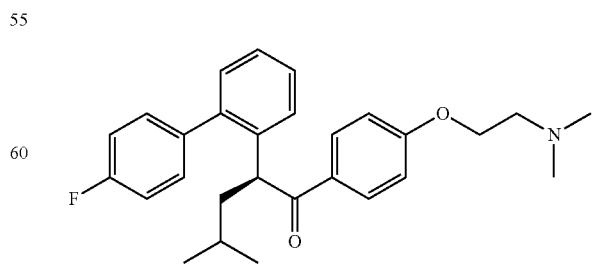

or the formula:

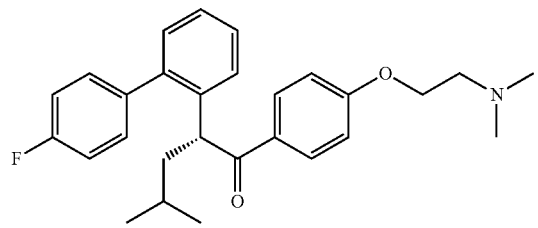

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Compounds of the present invention include compounds having the formula (II) or a pharmaceutically acceptable salt form thereof:

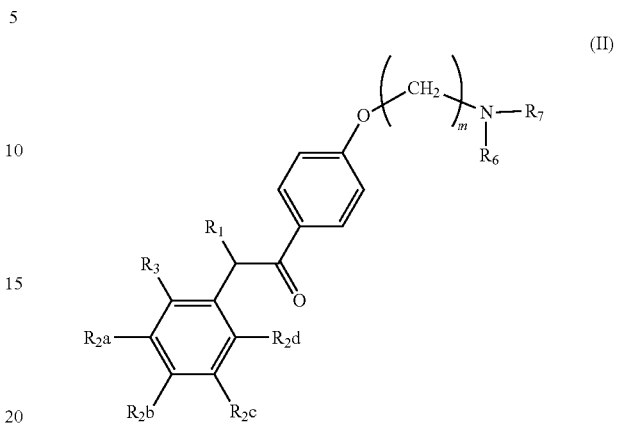

wherein non-limiting examples of $R^1$, $R^2$, $R^3$, $R^6$, $R^7$, and m are defined herein below in Table 1.

TABLE 1

Exemplary compounds of the formula (II)

| Entry | $R^1$ | $R^2a$ | $R^2b$ | $R^2c$ | $R^2d$ | $R^3$ | $R^6$ | $R^7$ | m |
|---|---|---|---|---|---|---|---|---|---|
| 1 | H | H | H | H | H | Ph | Me | Me | 2 |
| 2 | H | H | H | H | H | Ph | Me | Me | 3 |
| 3 | H | H | H | H | H | Ph | Me | Me | 4 |
| 4 | Et | H | H | H | H | Ph | Me | Me | 5 |
| 5 | Et | H | H | H | H | Ph | Me | Me | 6 |
| 6 | Et | H | H | H | H | Ph | Me | Me | 10 |
| 7 | i-Pr | H | H | H | H | Ph | Me | Me | 2 |
| 8 | i-Pr | H | H | H | H | Ph | Me | Me | 3 |
| 9 | i-Bu | H | H | H | H | Ph | Me | Me | 2 |
| 10 | i-Bu | H | H | H | H | Ph | Me | Me | 3 |
| 11 | i-Bu | H | H | H | H | Ph | Me | Et | 2 |
| 12 | i-Bu | H | H | H | H | Ph | n-hexyl | n-hexyl | 2 |
| 13 | i-Pr | H | H | H | H | Ph | —(CH$_2$)$_3$— | | 2 |
| 14 | i-Bu | H | H | H | H | Ph | —(CH$_2$)$_3$— | | 3 |
| 15 | i-pentyl | H | H | H | H | Ph | —(CH$_2$)$_4$— | | 2 |
| 16 | i-Pr | H | H | H | H | Ph | —(CH$_2$)$_2$—O—(CH$_2$)$_2$— | | 3 |
| 17 | i-Bu | H | H | H | H | Ph | —(CH$_2$)$_2$—NH—(CH$_2$)$_2$— | | 2 |
| 18 | i-pentyl | H | H | H | H | Ph | —(CH$_2$)$_2$—O—(CH$_2$)$_2$— | | 3 |
| 19 | cyclo-propyl | H | H | H | H | Ph | Me | Me | 2 |
| 20 | i-Pr | Cl | H | H | H | Ph | Me | Me | 2 |
| 21 | i-Bu | H | F | H | H | Ph | Me | Me | 2 |
| 22 | i-Pr | H | H | OCF$_3$ | H | Ph | Me | Me | 2 |
| 23 | n-Pr | CN | H | CH$_3$ | H | Ph | Me | Me | 2 |
| 24 | Cyclo-pentyl | H | H | H | H | Ph | Me | Me | 2 |
| 25 | Cyclo-hexyl | F | H | NO$_2$ | H | Ph | Me | Me | 2 |
| 26 | —CH$_2$—cyclo-hexyl | H | H | SO$_2$N(CH$_3$)$_2$ | H | Ph | Me | Me | 2 |
| 27 | 5-decyl | OCH$_3$ | H | H | OCH$_3$ | Ph | Me | Me | 2 |
| 28 | n-butyl | H | C(O)CH$_3$ | H | H | Ph | —(CH$_2$)$_4$— | | 3 |

Compounds of the present invention include compounds having the formula (III) or a pharmaceutically acceptable salt form thereof:

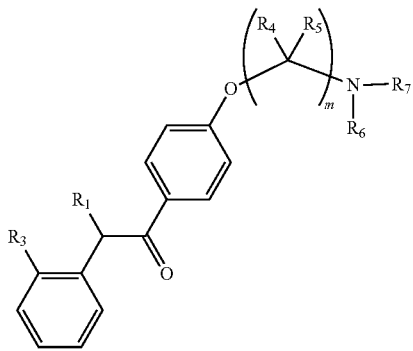

(III)

wherein non-limiting examples of $R^1$, $R^3$, $R^4$, $R^5$, $R^6$, $R^7$, and m are defined herein below in Table 2.

TABLE 2

Exemplary compounds of the formula (III)

| Entry | $R^1$ | $R^3$ | $R^4$ | $R^5$ | $R^6$ | $R^7$ | m |
|---|---|---|---|---|---|---|---|
| 1 | H | 2-pyridyl | H | H | Me | Me | 2 |
| 2 | H | 2-thienyl | H | H | Me | Me | 3 |
| 3 | H | 2-pyrizinyl | H | H | n-hexyl | n-hexyl | 2 |
| 4 | Et | 2-pyridyl | H | H | Me | Me | 2 |
| 5 | i-Pr | 3-pyridyl | H | H | Me | Me | 3 |
| 6 | i-Bu | 4-pyridyl | H | H | Me | Me | 4 |
| 7 | Cyclopropyl | 2-pyrimidinyl | H | H | Me | Me | 2 |
| 8 | 5-decyl | 2-furyl | H | H | Me | Me | 3 |
| 9 | cyclohexyl | 3-pyrrolyl | H | H | Me | Me | 2 |
| 10 | n-butyl | 2-thienyl | H | H | Me | Me | 2 |
| 11 | i-Pr | 1-naphthyl | H | H | Me | Me | 3 |
| 12 | i-Bu | 2-naphthyl | H | H | Me | Me | 2 |

TABLE 2-continued

Exemplary compounds of the formula (III)

| Entry | $R^1$ | $R^3$ | $R^4$ | $R^5$ | $R^6$ | $R^7$ | m |
|---|---|---|---|---|---|---|---|
| 13 | Cyclopropyl | 3-indolyl | H | H | Me | Me | 3 |
| 14 | Et | 5-quinolinyl | H | H | Me | Et | 4 |
| 15 | i-Pr | 5-tetrazolyl | H | H | n-hexyl | n-hexyl | 2 |
| 16 | i-Bu | 2-thiazolyl | H | H | —(CH$_2$)$_3$— | | 2 |
| 17 | i-Bu | 4-benzofuranyl | H | H | —(CH$_2$)$_3$— | | 3 |
| 18 | i-pentyl | 2-benzothiophenyl | H | H | —(CH$_2$)$_4$— | | 2 |
| 19 | i-Pr | 5-benzoimidazolyl | H | H | —(CH$_2$)$_2$—O—(CH$_2$)$_2$— | | 3 |
| 20 | 5-decyl | oxadiazolyl | H | H | CH$_3$ | n-Bu | 2 |

Compounds of the present invention include compounds having the formula (IV) or a pharmaceutically acceptable salt form thereof:

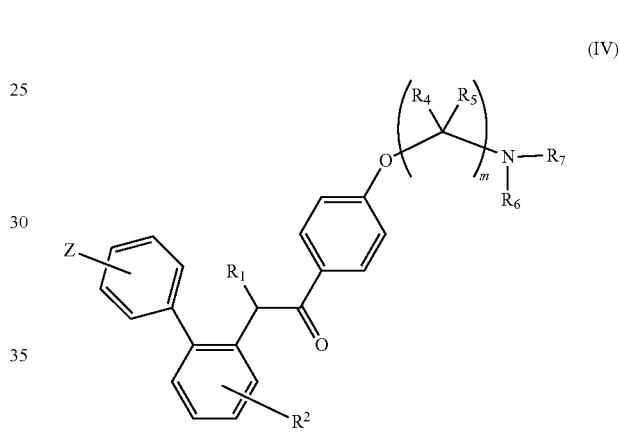

(IV)

wherein non-limiting examples of $R^1$, $R^2$, $R^4$, $R^5$, $R^6$, $R^7$, Z and m are defined herein below in Table 3.

TABLE 3

Exemplary compounds of the formula (IV)

| Entry | $R^1$ | $R^2$ | $R^4$ | $R^5$ | $R^6$ | $R^7$ | Z | m |
|---|---|---|---|---|---|---|---|---|
| 1 | H | 2-chloro | H | H | Me | Me | H | 2 |
| 2 | H | 3-CN | H | H | Me | Me | H | 3 |
| 3 | H | 4-OCH$_3$ | H | H | n-hexyl | n-hexyl | H | 2 |
| 4 | H | H | H | H | Me | Me | 4-NO$_2$ | 2 |
| 5 | i-Pr | H | H | H | Me | Me | 2-OCF$_3$ | 3 |
| 6 | i-Pr | 4-fluoro | H | H | Me | Me | H | 4 |
| 7 | i-Pr | 3-CN | H | H | Me | Me | Me | 2 |
| 8 | i-Pr | 3-chloro-5-CF$_3$ | H | H | Me | Me | 2-fluoro-4-CN | 3 |
| 9 | i-Bu | H | H | H | Me | Me | 3-SO$_2$N(CH$_3$)$_2$ | 2 |
| 10 | i-Bu | 4-F | H | H | Me | Me | H | 2 |
| 11 | i-Bu | 5-NO$_2$ | H | H | Me | Me | 3,5-dichloro | 3 |
| 12 | i-Bu | 2,4-difluoro | H | H | Me | Me | 3,4-dimethoxy | 2 |
| 13 | n-Bu | H | H | H | Me | Me | 3-C(O)CF$_3$ | 3 |
| 14 | n-Bu | 3-CF$_3$ | H | H | Me | Et | H | 4 |
| 15 | n-Bu | 4,5-dichloro | H | H | n-hexyl | n-hexyl | H | 2 |
| 16 | n-Bu | 4-fluoro-6-CN | H | H | —(CH$_2$)$_3$— | | 2-fluoro-4-methoxy | 2 |
| 17 | i-Bu | 4-benzofuranyl | H | H | —(CH$_2$)$_3$— | | | 3 |
| 18 | Cyclopropyl | H | H | H | —(CH$_2$)$_4$— | | 3-OCF$_3$ | 2 |
| 19 | Cyclopropyl | C(O)NH$_2$ | H | H | —(CH$_2$)$_2$—O—(CH$_2$)$_2$— | | H | 3 |
| 20 | Cyclopropyl | 4-CF$_3$ | H | H | CH$_3$ | n-Bu | 4-chloro | 2 |

TABLE 3-continued

Exemplary compounds of the formula (IV)

| Entry | $R^1$ | $R^2$ | $R^4$ | $R^5$ | $R^6$ | $R^7$ | Z | m |
|---|---|---|---|---|---|---|---|---|
| 21 | i-Bu | H | H | H | Me | M | F | 2 |
| 22 | —CH$_2$—cyclopropane | H | H | H | Me | Me | F | 2 |
| 23 | Et | H | H | H | Me | Me | F | 2 |
| 24 | n-Pr | H | H | H | Me | Me | F | 2 |
| 25 | Et | H | H | H | Me | H | F | 2 |
| 26 | n-Pr | H | H | H | Me | H | F | 2 |
| 27 | i-Bu | H | H | H | Me | H | F | 2 |

PROCESS

The present invention further relates to a process for preparing the functionalized N,N-dialkylamino phenyl ethers of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out. A given reaction can be carried out in one solvent or a mixture of more than one solvent. Depending on the particular reaction step, suitable solvents for a particular reaction step can be selected.

An aspect of the process of the present invention relates to a process for preparing the functionalized N,N-dialkylamino phenyl ethers of the present invention having the formula (I).

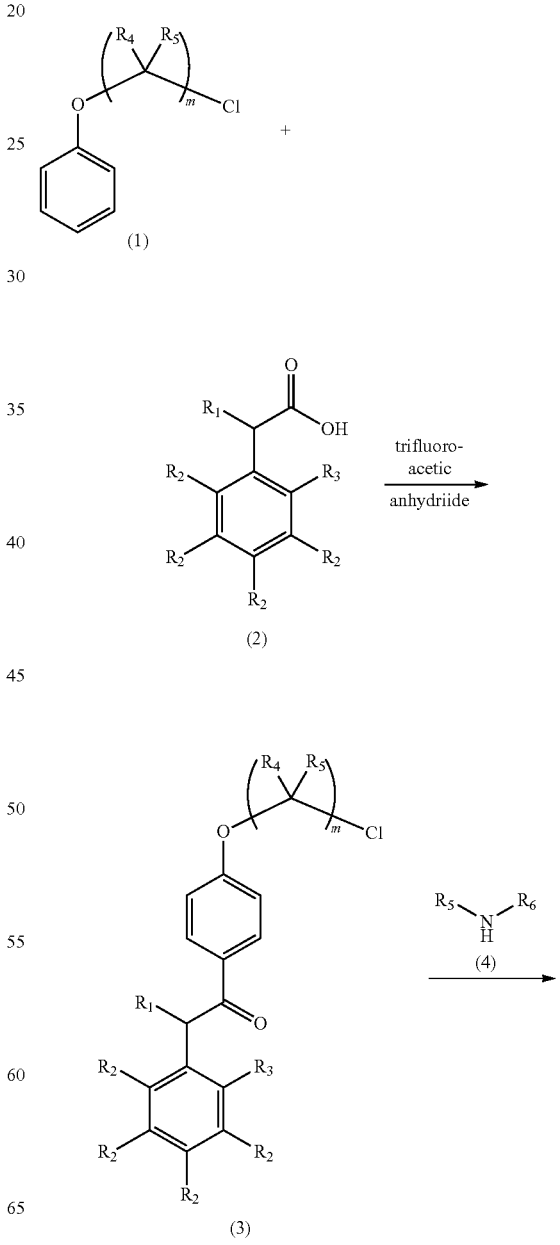

-continued

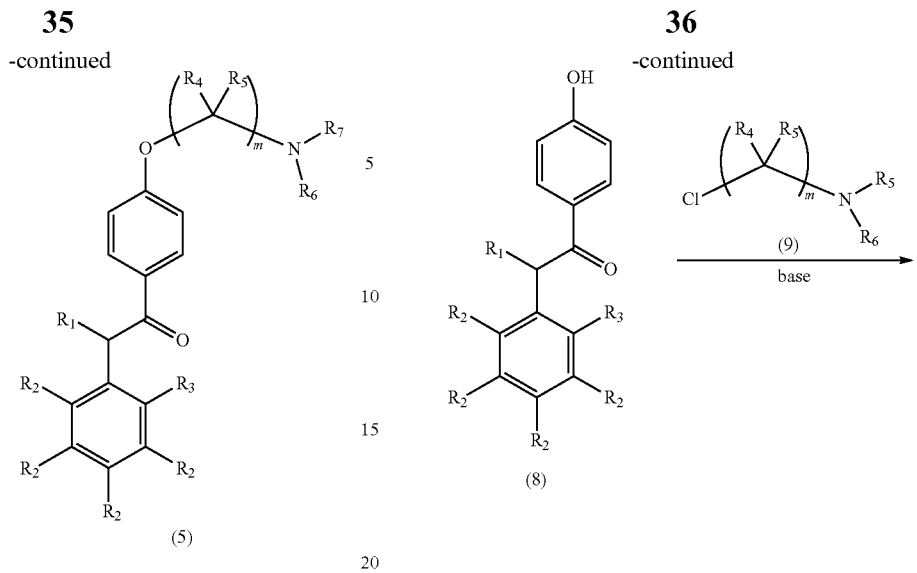

A compound of the formula (1), a known compound or a compound prepared by known methods, is reacted with a compound of formula (2), a known compound or a compound prepared by known methods, in the presence of 2,2,2-trifluoroacetic anhydride, optionally in the presence of a solvent such as benzene, toluene, tetrahydrofuran, 1,4-dioxane, methylene chloride, and the like, optionally with heating, optionally with microwave irradiation to provide a compound of the formula (3). A compound of the formula (3) is reacted with a compound of the formula (4), a known compound or a compound prepared by known methods, in the presence of a solvent such as methanol, ethanol, isopropanol, tetrahydrofuran, 1,4-dioxane, and the like, optionally in the presence of water, optionally with heating, optionally with microwave irradiation to provide a compound of the formula (5).

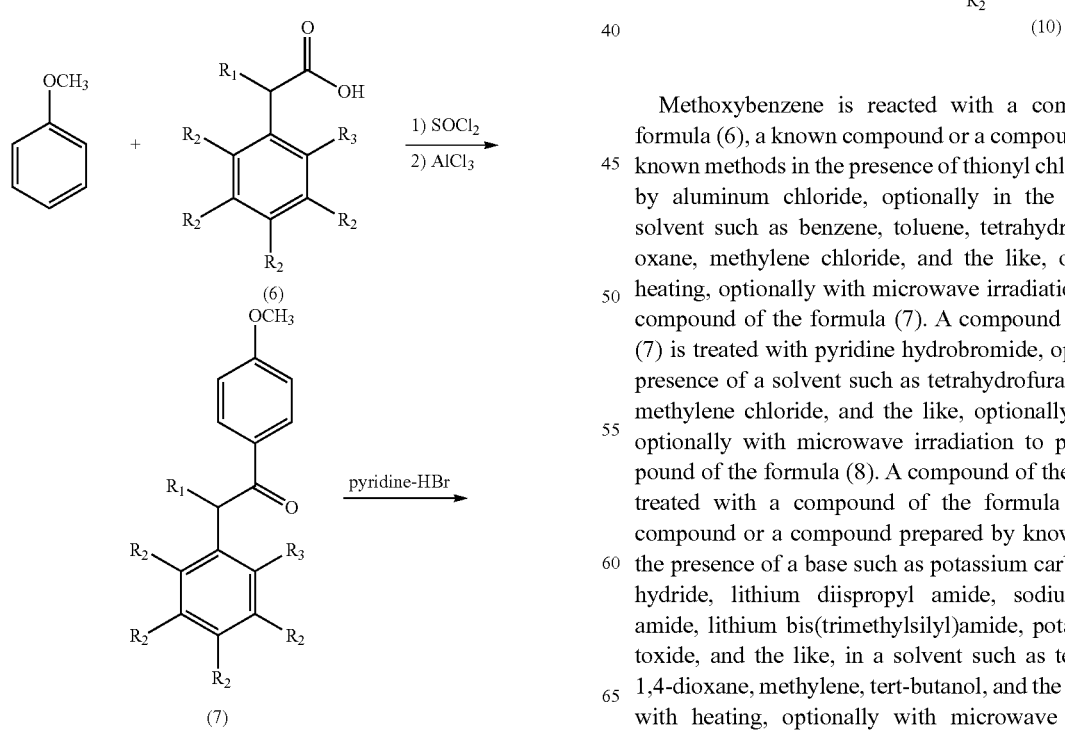

Methoxybenzene is reacted with a compound of the formula (6), a known compound or a compound prepared by known methods in the presence of thionyl chloride, followed by aluminum chloride, optionally in the presence of a solvent such as benzene, toluene, tetrahydrofuran, 1,4-dioxane, methylene chloride, and the like, optionally with heating, optionally with microwave irradiation to provide a compound of the formula (7). A compound of the formula (7) is treated with pyridine hydrobromide, optionally in the presence of a solvent such as tetrahydrofuran, 1,4-dioxane, methylene chloride, and the like, optionally with heating, optionally with microwave irradiation to provide a compound of the formula (8). A compound of the formula (8) is treated with a compound of the formula (9), a known compound or a compound prepared by known methods, in the presence of a base such as potassium carbonate, sodium hydride, lithium diisopropyl amide, sodium diisopropyl amide, lithium bis(trimethylsilyl)amide, potassium tert-butoxide, and the like, in a solvent such as tetrahydrofuran, 1,4-dioxane, methylene, tert-butanol, and the like, optionally with heating, optionally with microwave irradiation, to provide a compound of the formula (10).

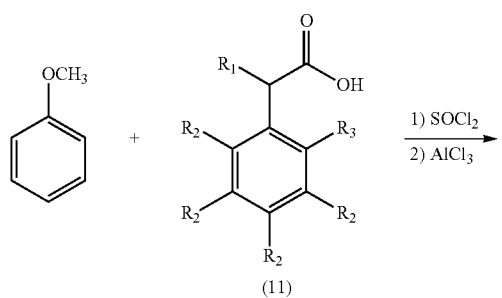

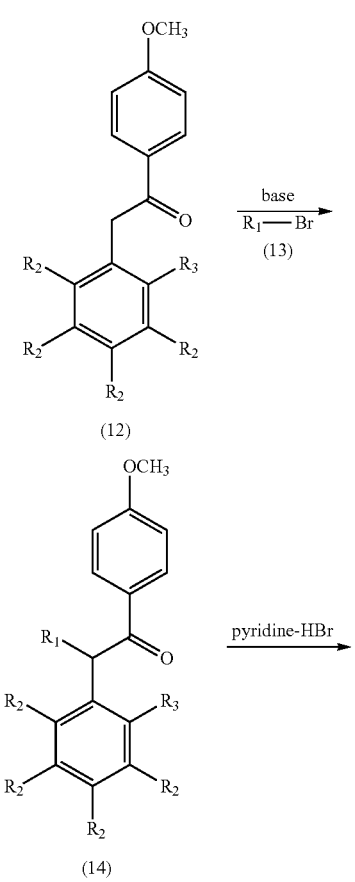

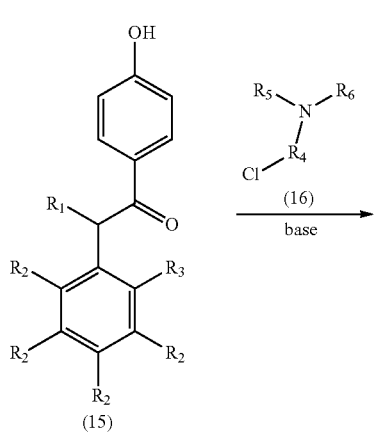

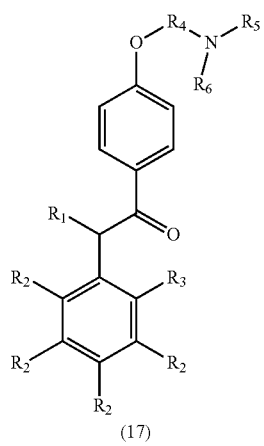

Methoxybenzene is reacted with a compound of the formula (11), a known compound or a compound prepared by known methods in the presence of thionyl chloride, followed by aluminum chloride, optionally in the presence of a solvent such as benzene, toluene, tetrahydrofuran, 1,4-dioxane, methylene chloride, and the like, optionally with heating, optionally with microwave irradiation to provide a compound of the formula (12). A compound of the formula (12) is reacted with a compound of the formula (13), a known compound or a compound prepared by known methods, in the presence of a base such as lithium diisopropyl amide, sodium isopropyl amide, sodium hydride, lithium bis(trimethylsilyl)amide, and the like, in a solvent such as tetrahydrofuran, 1,4-dioxane, methylene chloride, and the like, optionally with heating, optionally with microwave irradiation, to provide a compound of the formula (14). A compound of the formula (14) is reacted with pyridine hydrobromide, optionally in the presence of a solvent such as tetrahydrofuran, 1,4-dioxane, methylene chloride, and the like, optionally with heating, optionally with microwave irradiation to provide a compound of the formula (15). A compound of the formula (15) is reacted with a compound of the formula (16), a known compound or a compound prepared by known methods, in the presence of a base such as potassium carbonate, sodium hydride, lithium diispropyl amide, sodium diisopropyl amide, lithium bis(trimethylsilyl) amide, potassium tert-butoxide, and the like, in a solvent such as tetrahydrofuran, 1,4-dioxane, methylene, tert-butanol, and the like, optionally with heating, optionally with microwave irradiation, to provide a compound of the formula (17).

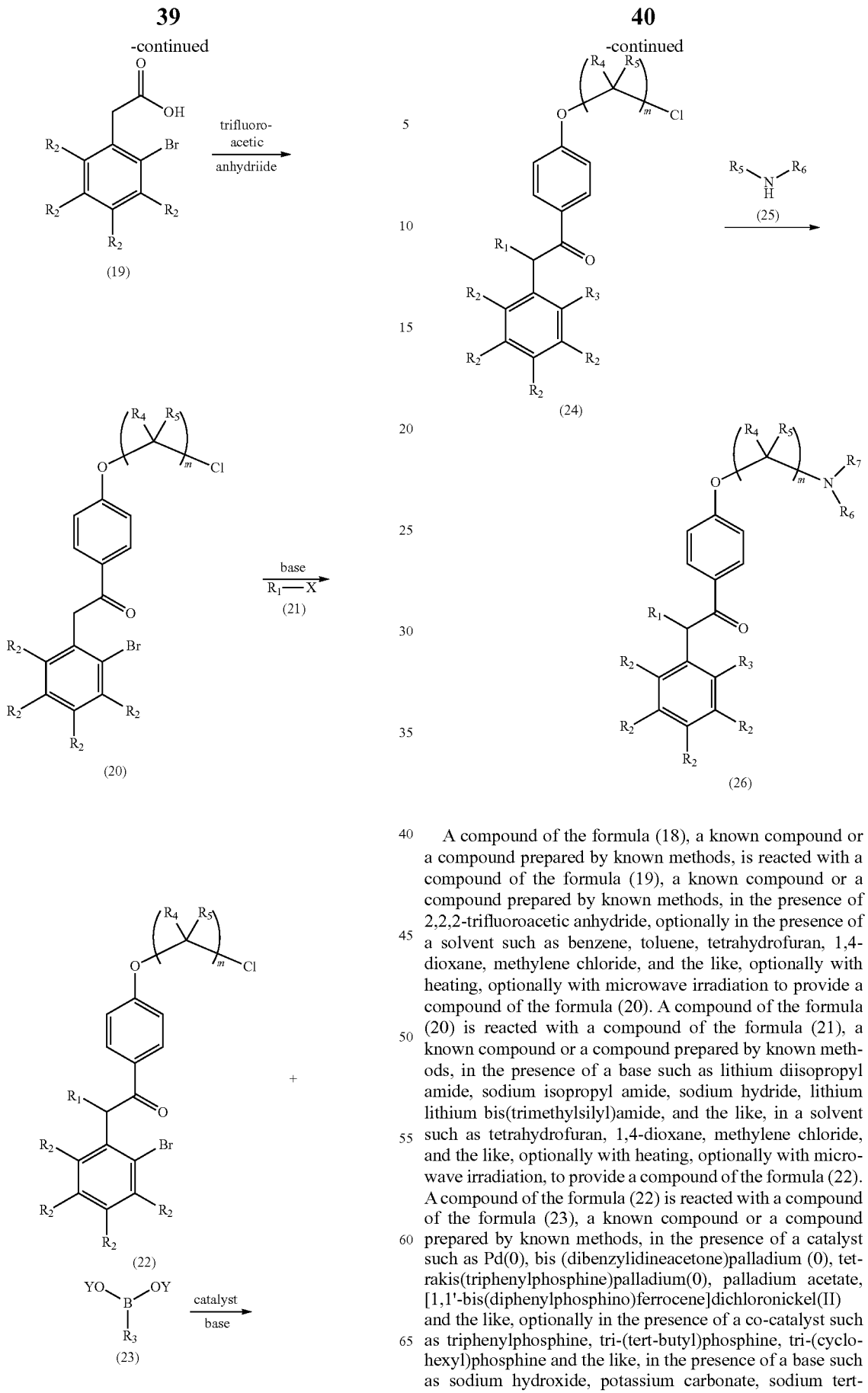

A compound of the formula (18), a known compound or a compound prepared by known methods, is reacted with a compound of the formula (19), a known compound or a compound prepared by known methods, in the presence of 2,2,2-trifluoroacetic anhydride, optionally in the presence of a solvent such as benzene, toluene, tetrahydrofuran, 1,4-dioxane, methylene chloride, and the like, optionally with heating, optionally with microwave irradiation to provide a compound of the formula (20). A compound of the formula (20) is reacted with a compound of the formula (21), a known compound or a compound prepared by known methods, in the presence of a base such as lithium diisopropyl amide, sodium isopropyl amide, sodium hydride, lithium lithium bis(trimethylsilyl)amide, and the like, in a solvent such as tetrahydrofuran, 1,4-dioxane, methylene chloride, and the like, optionally with heating, optionally with microwave irradiation, to provide a compound of the formula (22). A compound of the formula (22) is reacted with a compound of the formula (23), a known compound or a compound prepared by known methods, in the presence of a catalyst such as Pd(0), bis (dibenzylidineacetone)palladium (0), tetrakis(triphenylphosphine)palladium(0), palladium acetate, [1,1'-bis(diphenylphosphino)ferrocene]dichloronickel(II) and the like, optionally in the presence of a co-catalyst such as triphenylphosphine, tri-(tert-butyl)phosphine, tri-(cyclohexyl)phosphine and the like, in the presence of a base such as sodium hydroxide, potassium carbonate, sodium tert-butoxide, n-butyl lithium, potassium phosphate, cesium carbonate, potassium fluoride on alumina and the like, optionally in the presence of a solvent like methanol, toluene, tetrahydrofuran, 1,4-dioxane, dimethylformamide and the like, optionally in the presence of water, optionally with heating, optionally with microwave irradiation, to provide a compound of the formula (24). A compound of the formula (24) is reacted with a compound of the formula (25), a known compound or a compound prepared by known methods, in the presence of a solvent such as methanol, ethanol, isopropanol, tetrahydrofuran, 1,4-dioxane, and the like, optionally in the presence of water, optionally with heating, optionally with microwave irradiation to provide a compound of the formula (26).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

Example 1: Synthesis of 1-(4-(2-(Dimethylamino)ethoxy)phenyl)-2-(4'-fluoro-[1,1'-biphenyl]-2-yl)ethanone (MC-290042)

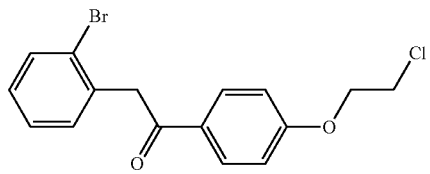 [SMILES: O=C(Cc1ccccc1Br)c1ccc(OCCCl)cc1]

Step 1: 2-(2-Bromophenyl)-1-(2-chloroethoxy)phenyl)ethanone

2-Bromophenyl acetic acid (5.0 g, 23.3 mmol) was suspended in trifluoroacetic anhydride (15 mL, 104 mmol). Chloroethyoxylbenzene (3.2 mL, 23.3 mmol) was added to the stirred suspension dropwise. The resulting mixture was allowed to stir overnight at room temperature. The reaction was quenched with saturated aqueous sodium bicarbonate solution and then extracted with ethyl acetate (2×50 mL). The combined organic layers were dried over anhydrous magnesium sulfate and concentrated on a rotary evaporator. The resulting residue was purified by chromatography on silica gel (gradient of ethyl acetate in hexane) to afford 2.7 g (33%) of the desired product as a light orange solid. $^1$H NMR (400 MHz, CDCl$_3$) δ 8.05 (d, J=8.9 Hz, 2H), 7.60 (d, J=8.5 Hz, 1H), 7.24 (m, 2H), 7.18 (m, 1H), 6.96 (d, J=9.0 Hz, 2H), 4.40 (s, 2H), 4.37 (t, J=5.5 Hz, 2H), 3.88 (t, J=5.7 Hz, 2H); MS [ESI, (M+H)$^+$]. 354/356.

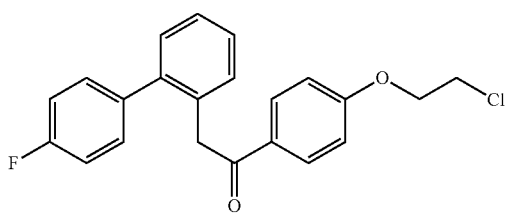 [SMILES: O=C(Cc1ccccc1-c1ccc(F)cc1)c1ccc(OCCCl)cc1]

Step 2: 1-(4-(2-Chloroethoxy)phenyl]-2-(4'-fluoro-[1,1'-biphenyl]-2-yl)ethanone 2-(2-Bromophenyl)-1-(2-chloro-ethoxy)phenyl)ethanone (1.0 g, 2.83 mmol), 4-fluorophenylboronic acid (0.791 g, 5.66 mmol), anhydrous potassium fluoride (0.539 g, 9.3 mmol) and tris(dibenzylideneacetone)dipalladium(0) (0.128 g, 0.140 mmol) were added to 40 mL vial fitted with a septa cap under nitrogen. The vial was sealed and purged with nitrogen for 5 minutes. tetrahydrofuran (5 mL) was added, and the mixture was purged for an additional 5 minutes. A solution of tri-tert-butylphosphine (10 wt % in hexanes; 1.45 mL, 4.91 mmol) was added via syringe, and the mixture was vigorously stirred at 60° C. for 16 hours. The mixture diluted with 15 mL of ethyl acetate, filtered through a plug silica gel. The silica gel was washed with 50 mL of ethyl acetate, and the combined filtrates were concentrated on a rotary evaporator to give a crude brown oil. The resulting residue was purified by chromatography on silica gel (gradient of ethyl acetate in hexane) to provide 350 mg (34%) of the desired product as a white solid. $^1$H NMR (400 MHz, CDCl$_3$) δ 7.8 (d, J=9.0 Hz, 2H), 7.3 (m, 6H), 7.05 (m, 2H), 6.9 (d, J=9.0 Hz, 2H), 4.29 (t, J=6 Hz, 2H), 4.19 (s, 2H), 3.84 (t, J=6 Hz, 2H); MS [ESI, (M+H)+] 369.

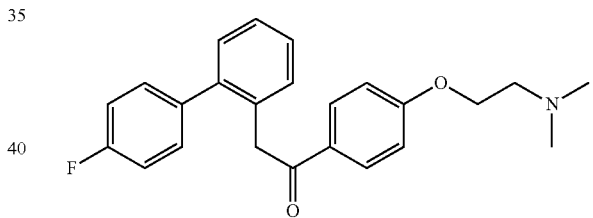

Step 3: 1-(4-(2-(Dimethylamino)ethoxy)phenyl)-2-(4'-fluoro-[1,1'-biphenyl]-2-yl)ethanone 1-[4-(2-Chloro-ethoxy)-phenyl]-2-(4'-fluoro-biphenyl-2-yl)-ethanone (0.300 g, 0.81 mmol) was suspended in 40% aqueous dimethylamine (10 mL) and ethanol (5 mL) and stirred at 60° C. for 16 hours. The reaction mixture was cooled and then concentrated on a rotary evaporator. The resulting residue was dissolved in ethyl acetate and filtered through 4 g of silica gel and the title compound was eluted off with dichloromethane/5% methanol ammonia to provide crude title compound. The resulting crude product was purified by chromatography on silica gel (gradient of ethyl acetate in hexane) to provide 150 mg (49%) of the desired product as a clear colorless oil (43%). $^1$H NMR (400 MHz, CDCl$_3$) δ 7.79 (d, J=8.8 Hz, 2H), 7.30 (m, 6H), 7.05 (m, 2H), 6.90 (d, J=8.8 Hz, 2H), 4.2 (s, 2H), 4.15 (t, J=5.6 Hz, 2H), 2.81 (t, J=5.6, 2H), 2.39 (s, 2H); MS [ESI, (M+H)+] 378.

Example 2: Synthesis of 2-(2'-Chloro-[1,1'-biphenyl]-2-yl)-1-(4-(2-(dimethylamino)ethoxy)phenyl)ethanone (MC-290063)

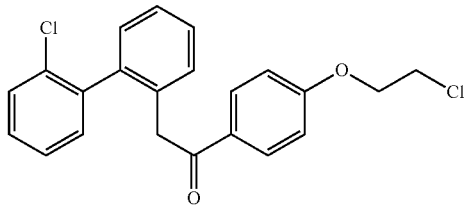 [SMILES: O=C(Cc1ccccc1-c1ccccc1Cl)c1ccc(OCCCl)cc1]

Step 1: 2-(2'-Chloro-[1,1'-biphenyl]-2-yl)-1-(4-(2-chloroethoxy)phenyl)ethanone 2-(2-Bromophenyl)-1-(2-chloroethoxy)phenyl)ethanone (0.500 g, 1.41 mmol), 2-chlorophenylboronic acid (0.440 g, 2.82 mmol), anhydrous potassium fluoride (0.266 g, 4.6 mmol) and tris(dibenzylideneacetone)dipalladium(0) (0.164 g, 0.069 mmol) were added to 40 mL vial fitted with a septa cap under nitrogen. The vial was sealed and purged with nitrogen for 5 minutes. tetrahydrofuran (5 mL) was added, and the mixture was purged for an additional 5 minutes. A solution of tri-tert-butylphosphine (10 wt % in hexanes; 0.63 mL, 0.207 mmol) was added via syringe, and the mixture was vigorously stirred at 60° C. for 16 hours. The mixture diluted with 15 mL of ethyl acetate and filtered through a plug silica gel. The silica gel was washed with 50 mL of ethyl acetate, and the resulting combined filtrates were concentrated on a rotary evaporator to give a crude brown oil. The resulting residue was purified by chromatography on silica gel (gradient of ethyl acetate in hexane) to provide 162 mg (30%) of the desired product as a white solid. $^1$H NMR (400 MHz, CDCl$_3$) δ 7.75 (d, J=9.0 Hz, 2H), 7.34 (m, 8H), 6.86 (d, J=9.0 Hz, 2H), 4.26 (t, J=5.8 Hz, 2H), 4.07 (dd, J=28 Hz, J=16 Hz, 2H), 3.84 (t, J=5.8 Hz, 2H), MS [ESI, (M+H)$^+$] 385.

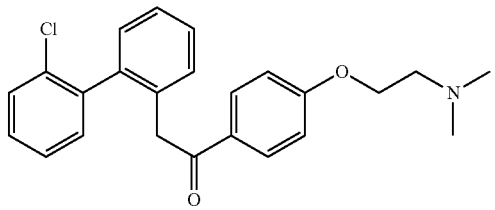 [SMILES: CN(C)CCOc1ccc(C(=O)Cc2ccccc2-c2ccccc2Cl)cc1]

Step 2: 2-(2'-Chloro-[1,1'-biphenyl]-2-yl)-1-(4-(2-(dimethylamino)ethoxy)phenyl)ethanone 2-(2'-Chloro-biphenyl-2-yl)-1-[4-(2-chloro-ethoxy)-phenyl]-ethanone (0.160 g, 0.42 mmol) was suspended in 40% aqueous dimethylamine (10 mL) and ethanol (5 mL) and stirred at 60° C. for 16 hours. The reaction mixture was cooled and then concentrated on a rotary evaporator. The resulting residue was dissolved in ethyl acetate and filtered through 4 g of silica gel and the title compound was eluted off with dichloromethane/5% methanol ammonia to provide crude title compound. The crude product was purified by reversed phase chromatography (gradient of acetonitrile 0.1% TFA/water 0.1% TFA) to provide 70 mg (42%) of the desired product as a clear colorless oil. $^1$H NMR (400 MHz, CDCl$_3$) δ 7.64 (d, J=8.8 Hz, 2H), 7.36 (m, 1H), 7.26 (m, 3H), 7.16 (m, 4H), 6.76 (d, J=8.8 Hz, 2H), 4.04 (t, J=5.6 Hz, 2H), 3.97 (dd, J=27 Hz, J=16 Hz, 2H), 2.7 (t, J=5.6 Hz, 2H), 2.29 (s, 2H); MS [ESI, (M+H)+]394.

Example 3. Synthesis of 1-(4-(2-(dimethylamino)ethoxy)phenyl)-2-(4'-fluoro-[1,1'-biphenyl]-2-yl)-4-methylpentan-1-one (MC-290284)

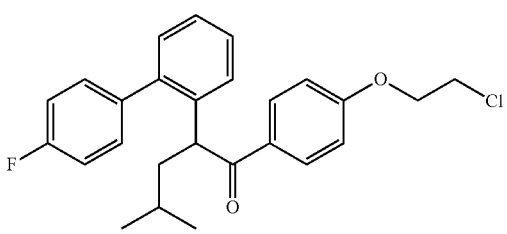 [SMILES: CC(C)CC(C(=O)c1ccc(OCCCl)cc1)c1ccccc1-c1ccc(F)cc1]

Step 1. 2-(2-Bromophenyl)-1-(4-(2-chloroethoxy)phenyl)-4-methylpentan-1-one To a solution of 2-(2-bromophenyl)-1-(2-chloroethoxy) phenyl) ethan-1-one (1.0 g, 2.82 mmol) in dry tetrahydrofuran (15 mL) at room temperature was added sodium hydride (0.115 g, 3 mmol, 60% suspension in mineral oil) portionwise. After stirring 30 minutes, iodo-2-methylpropane (0.65 mL, 5.7 mmol) was added via syringe. After 16 hours at 40° C., the mixture was poured into saturated aqueous ammonium chloride solution and extracted with diethyl ether (×2), dried over anhydrous magnesium sulfate and evaporated. The resulting residue was purified by chromatography on silica gel (gradient of ethyl acetate in hexane) to provide 450 mg (39%) of the desired product as a clear oil. $^1$H NMR (400 MHz, CDCl$_3$) δ 7.92 (d, J=9.0 Hz, 2H), 7.5 (dd, J=8 Hz, J=1.2 Hz, 1H), 7.17 (dd, J=8 Hz, J=2 Hz, 1H), 7.11, (m, 1H), 6.97 (m, 1H), 6.82 (d, J=9.0 Hz, 2H), 5.06 (dd, J=8.7 Hz, J=5.4 Hz, 1H), 4.17 (t, J=5.9 Hz, 2H), 3.72 (t, J=5.9 Hz, 2H), 2.05 (m, 1H), 1.42 (m, 1H), 1.40 (m, 1H), 0.89 (d, J=6.5 Hz, 3H), 0.86 (d, J=6.5 Hz, 3H); MS [ESI, (M+H)+] 411.

Step 2. 1-(4-(2-chloroethoxy)phenyl)-2-(4'-fluoro-[1,1'-biphenyl]-2-yl)-4-methylpentan-1-one 2-(2-Bromophenyl)-1-(4-(2-chloroethoxy)phenyl)-4-methylpentan-1-one (1.3 g, 3.17 mmol), 4-fluoro-phenylboronic acid (0.440 g, 2.82 mmol), anhydrous potassium fluoride (1.85 g, 32 mmol), and tris(dibenzylidineacetone)acetonedipalladium(0) (0.280 g, 0.306 mmol) were added to a 40 mL vial fitted with a septum cap under nitrogen. The vial was sealed and purged with nitrogen for 5 minutes. Anhydrous tetrahydrofuran (5 mL) was added, and the mixture was purged for an additional 5 minutes. A solution of tri-tert-butylphosphine (10 wt % in hexanes; 2.72 mL, 0.918 mmol) was added via syringe, and the mixture was vigorously stirred at 60° C. for 16 hours. The mixture diluted with 15 mL of ethyl acetate and filtered through a plug silica gel. The silica gel plug was washed with 50 mL of ethyl acetate and the combined filtrates were concentrated on a rotary evaporator to give a crude brown oil. The resulting residue was purified by chromatography on silica gel (gradient of ethyl acetate in hexane) to provide 0.550 mg (41%) of the desired product as a clear oil. $^1$H NMR (400 MHz, CDCl$_3$) δ 7.47 (d, J=9.0 Hz, 2H), 7.38 (dd, J=8 Hz, J=1.1 Hz, 1H), 7.12 (m, 7H), 6.69 (d, J=9.0 Hz, 2H), 4.65 (dd, J=9.4, J=4.2 Hz, 1H), 4.15 (t, J=5.9 Hz, 2H), 3.72 (t, J=5.9 Hz, 2H), 2.24 (m, 1H), 1.45 (m, 2H), 0.76 (d, J=6.4 Hz, 3H), 0.68 (d, 6.4 Hz, 3H); MS [ESI, (M+H)+] 425.

Step 3. 1-(4-(2-(Dimethylamino)ethoxy)phenyl)-2-(4'-fluoro-[1,1'-biphenyl]-2-yl)-4-methylpentan-1-one

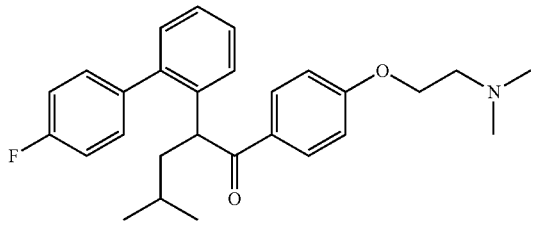

1-(4-(2-Chloroethoxy)phenyl)-2-(4'-fluoro-[1,1'-biphenyl]-2-yl)-4-methylpentan-1-one (0.250 g, 0.61 mmol) was suspended in a mixture of 40% aqueous dimethylamine (10 mL) and ethanol (5 mL) and stirred at 65° C. 16 hours. The reaction mixture was cooled and then concentrated on a rotary evaporator. The resulting residue was dissolved in ethyl acetate and loaded onto a 4 g of silica gel column, which was then eluted with 7 N ammonia in methanol (5%)/dichloromethane to provide crude title compound. The resulting oil was purified by reversed phase chromatography (gradient of acetonitrile in water with 0.1% trifluoroacetic acid modifier) to provide 35 mg (13%) of the desired product as a clear colorless oil. $^1$H NMR (400 MHz, CDCl$_3$) δ 7.46 (d, J=9 Hz, 2H), 7.39 (dd, J=8 Hz, J=1.1 Hz, 1H), 7.12 (m, 7H), 6.7 (d, J=9 Hz, 2H), 4.65 (dd, J=9 Hz, J=4.2 Hz, 1H), 4.02 (t, J=5.6 Hz, 2H), 2.69 (t, J=5.6 Hz, 2H), 2.28 (s, 6H), 2.24 (m, 1H), 1.44 (m, 2H) 0.76 (d, J=6.4 Hz, 3H), 0.69 (d, J=6.4 Hz, 3H); MS [ESI, (M+H)+] 434.

Example 4. Synthesis of 3-cyclopropyl-1-(4-(2-(dimethylamino)ethoxy)phenyl)-2-(4'-fluoro-[1,1'-biphenyl]-2-yl)propan-1-one (MC-290295)

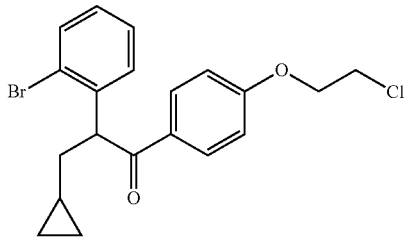 [SMILES: O=C(c1ccc(OCCCl)cc1)C(CC1CC1)c1ccccc1Br]

Step 1. 2-(2-Bromophenyl)-1-(4-(2-chloroethoxy)phenyl)-3-cyclopropylpropan-1-one To a solution of 2-(2-bromophenyl)-1-(2-chloroethoxy)phenyl) ethan-1-one (2.0 g, 5.64 mmol) in dry tetrahydrofuran (15 mL) at room temperature was added sodium hydride (0.230 g, 6 mmol, 60% suspension in mineral oil) portionwise. After stirring 30 minutes, iodomethyl cyclopropane (1.25 g, 7 mmol) was added via syringe. After 16 hours at 40° C., the mixture was poured into saturated aqueous ammonium chloride solution and extracted with diethyl ether (×2), dried over anhydrous magnesium sulfate and evaporated. The resulting residue was purified by chromatography on silica gel (gradient if ethyl acetate in hexane) to provide 940 mg (41%) of the desired product as a clear oil. $^1$H NMR (400 MHz, CDCl$_3$) δ 7.89 (d, J=9.0 Hz, 2H), 7.47 (dd, J=7.9 Hz, J=1 Hz, 1H), 7.09 (m, 3H), 6.94 (m, 1H), 6.79 (d, J=9.0 Hz, 1H), 5.48 (dd, J=7.8 Hz, J=6.2 Hz, 1H), 4.14 (t, J=5.9 Hz, 2H), 3.69 (dd, J=5.9 Hz, 2H), 2.08 (m, 1H), 1.35 (m, 1H), 0.64 (m, 1H), 0.32 (m, 1H), 0.25 (m, 1H), 0.0 (m, 1H), −0.05 (m, 1H); MS [ESI, (M+H)+]409.

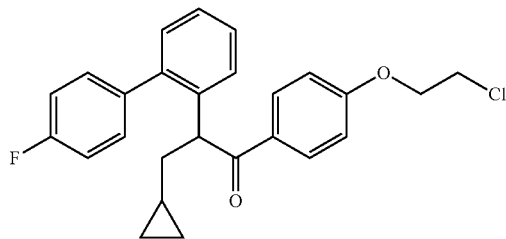 [SMILES: O=C(c1ccc(OCCCl)cc1)C(CC1CC1)c1ccccc1-c1ccc(F)cc1]

Step 2. 1-(4-(2-Chloroethoxy)phenyl)-3-cyclopropyl-2-(4'-fluoro-[1,1'-biphenyl]-2-yl)propan-1-one 2-(2-bromophenyl 1-(4-(2-chloroethyoxy)phenyl) 3-cyclopropylpropan-1-one (0.930 g, 2.29 mmol), 2-fluoro-phenylboronic acid (1.76 g, 12.68 mmol), anhydrous potassium fluoride (1.85 g, 32 mmol), and tris(dibenzylideneacetone)dipalladium(0) (0.280 g, 0.306 mmol) were added to 40 mL vial fitted with a septa cap under nitrogen. The vial was sealed and purged with nitrogen for 5 minutes. Anhydrous tetrahydrofuran (5 mL) was added, and the mixture was purged for an additional 5 minutes. A solution of tri-tert-butylphosphine (10 wt % in hexanes; 2.72 mL, 0.918 mmol) was added via syringe, and the mixture was vigorously stirred at 60° C. for 16 hours. The mixture diluted with 15 mL of ethyl acetate and filtered through a plug silica gel. The silica plug was washed with 50 mL of ethyl acetate and the combined filtrates were concentrated on a rotary evaporator to give a crude brown oil. The resulting residue was purified by chromatography on silica gel (gradient of ethyl acetate in hexane) to provide 0.500 g (52%) of the desired product as a white solid. $^1$H NMR (400 MHz, CDCl$_3$) δ 7.45 (d, J=9.0 Hz, 2H), 7.36 (dd, J=8.0 Hz, J=1.2 Hz, 1H), 7.15 (m, 7H), 6.65 (d, J=9.0 Hz, 2H), 4.40 (dd, J=8.8 Hz, J=5.0 Hz, 1H), 4.18 (t, J=6.1 Hz, 2H), 3.70 (t, J=6.1 Hz, 2H), 2.25 (m, 1H), 1.63 (m, 1H); 0.71 (m, 1H), 0.39 (m, 2H), 0.12 (m, 1H), 0.00 (m, 1H); MS [ESI, (M+H)+] 445.

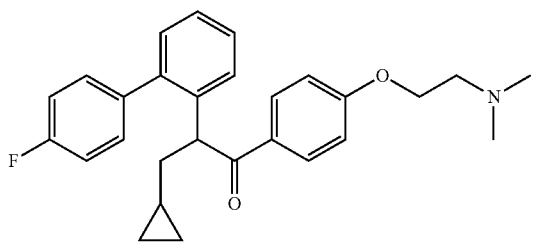 [SMILES: CN(C)CCOc1ccc(C(=O)C(CC2CC2)c2ccccc2-c2ccc(F)cc2)cc1]

Step 3. 3-Cyclopropyl-1-(4-(2-(dimethylamino) ethoxy)phenyl)-2-(4'-fluoro-[1,1'-biphenyl]-2-yl) propan-1-one 1-(4-(2-chloroethoxy)phenyl)-3-cyclopropyl-2-(4'-fluoro-[1,1'-biphenyl]-2-yl)propan-1-one (0.150 g, 0.36 mmol) was suspended in a mixture of 40% aqueous dimethylamine (10 mL) and ethanol (5 mL) and stirred at 65° C. 16 hours. The reaction mixture was cooled and then concentrated on a rotary evaporator. The resulting residue was dissolved in ethyl acetate and loaded onto a 4 g of silica gel column and eluted with 7 N ammonia in methanol (5%)/ dichloromethane to provide crude title compound. The resulting oil was purified by reversed phase chromatography (gradient of acetonitrile in water with 0.1% trifluoroacetic acid modifier) to provide 35 mg (40%) of the desired product as a clear colorless oil (65%). $^1$H NMR (400 MHz, CDCl$_3$) δ 7.59 (d, J=9.0 Hz, 2H), 7.52 (dd, J=8 Hz, J=1.1 Hz, 1H), 7.33 (m, 3H), 7.24 (m, 4H), 6.81 (d, J=9.0 Hz, 2H), 4.82 (dd, J=8.9 Hz, J=5.2 Hz, 1H), 4.16 (t, J=5.6 Hz, 2H), 2.86 (t, J=5.4 Hz, 2H); 2.44 (s, 6H), 2.35 (m, 1H), 1.63 (m, 1H); 0.71 (m, 1H), 0.39 (m, 2H), 0.12 (m, 1H), 0.00 (m, 1H); MS [ESI, (M+H)+] 411.

Example 5. Synthesis of 1-(4-(2-(dimethylamino) ethoxy)phenyl)-2-(4'-fluoro-[1,1'-biphenyl]-2-yl) butan-1-one (MC-290290)

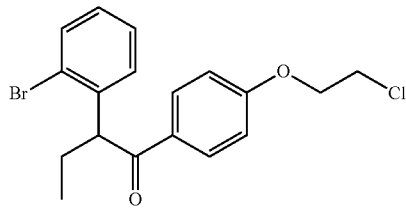 [SMILES: CCC(C(=O)c1ccc(OCCCl)cc1)c1ccccc1Br]

Step 1. 2-(2-Bromophenyl)-1-(4-(2-chloroethoxy) phenyl) butan-1-one

To a solution of 2-(2-bromophenyl)-1-(2-chloroethoxy) phenyl) ethan-1-one (2.0 g, 5.66 mmol) in dry tetrahydrofuran (15 mL) at room temperature was added sodium hydride (0.239 g, 6.0 mmol, 60% suspension in mineral oil) portionwise. After stirring 30 minutes, iodoethane (0.48 mL, 6.0 mmol) was added via syringe. After 16 hours at 40° C., the mixture was poured into saturated aqueous ammonium chloride solution and extracted with diethyl ether (×2), dried over anhydrous magnesium sulfate and evaporated. The resulting residue was purified by chromatography on silica gel (gradient of ethyl acetate in hexane) to provide 2.0 g (92%) of the desired product as a clear oil. $^1$H NMR (400 MHz, CDCl$_3$) δ 7.99 (d, J=9.0 Hz, 2H), 7.60 (d, J=8.6 Hz, 1H), 7.21 (m, 2H), 7.1 (m, 1H), 6.91 (d, J=9.0 Hz, 2H), 4.95 (dd, J=7.4 Hz, J=6.68, 1H), 4.26 (t, J=5.8 Hz, 2H), 3.81 (t, J=5.8 Hz, 2H), 2.17 (m, 2H), 1.8 (m, 2H), 0.98 (t, J=7.5 Hz, 3H), MS [ESI, (M+H)+] 383.

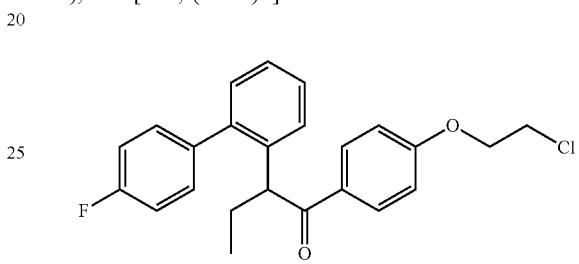

Step 2. 1-(4-(2-Chloroethoxy)phenyl)-2-(4'-fluoro-[1,1'-biphenyl]-2-yl) butan-1-one 2-(2-Bromophenyl)-1-(4-(2-chloroethoxy) phenyl) butan-1-one (2.0 g, 5.24 mmol), 4-fluorophenylboronic acid (3.3 g, 24 mmol), anhydrous potassium fluoride (3.48 g, 60 mmol) and tris(dibenzylideneacetone)dipalladium(0) (0.280 g, 0.306 mmol) were added to 40 mL vial fitted with a septa cap under nitrogen. The vial was sealed and purged with nitrogen for 5 minutes. Anhydrous tetrahydrofuran (25 mL) was added, and the mixture was purged for an additional 5 minutes. A solution of tri-tert-butylphosphine (10 wt % in hexanes; 2.72 mL, 0.0918 mmol) was added via syringe, and the mixture was vigorously stirred at 60° C. for 16 hours. The mixture diluted with 15 mL of ethyl acetate and filtered through a plug silica gel. The silica plug was washed with 50 mL of ethyl acetate and the combined filtrates were concentrated on a rotary evaporator to give a crude brown oil. The resulting residue was purified by chromatography on silica gel (gradient of ethyl acetate in hexane) to provide 1.3 g (63%) of the desired product as a white solid. $^1$H NMR (400 MHz, CDCl$_3$) δ 7.44 (d, J=9.0 Hz, 2H), 7.35 (dd, J=8.1 Hz, J=1.1 Hz, 1H), 7.13 (m, 7H), 6.67 (d, J=9.0 Hz, 2H), 4.42 (dd, J=9 Hz, J=5.1 Hz, 1H), 4.15 (t, J=6 Hz, 2H), 3.72 (t, J=6 Hz, 2H), 2.25 (m, 1H), 1.74 (m, 1H), 0.81 (t, J=7.3 Hz, 3H); MS [ESI, (M+H)+] 396.

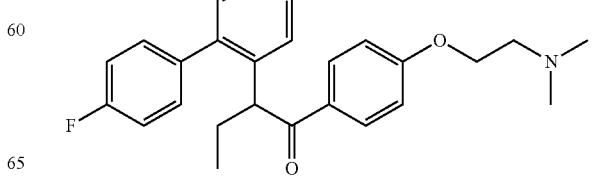

Step 3. 1-(4-(2-(dimethylamino)ethoxy)phenyl)-2-(4'-fluoro-[1,1'-biphenyl]-2-yl)butan-1-one 1-[4-(2-Chloro-ethoxy)-phenyl]-2-(4'-fluoro-biphenyl-2-yl)-ethanone (0.200 g, 0.51 mmol) was suspended in 40% aqueous dimethylamine (10 mL) and ethanol (5 mL) and stirred at 65° C. 16 hours. The reaction mixture was cooled and then concentrated on a rotary evaporator. The resulting residue was dissolved in ethyl acetate and loaded onto a 4 g of silica gel column and eluted off with 7 N ammonia in methanol (5%)/dichloromethane to provide crude title compound. The resulting oil was purified by reversed phase chromatography (gradient of acetonitrile in water with 0.1% trifluoroacetic acid modifier) to provide 100 mg (48%) of the desired product as a clear colorless oil. $^1$H NMR (400 MHz, CDCl$_3$) δ 7.43 (d, J=9 Hz, 2H), 7.36 (dd, J=8 Hz, J=1.2 Hz, 1H), 7.14 (m, 7H), 6.7 (d, J=9 Hz, 2H), 4.42 (dd, J=9 Hz, J=5.2 Hz, 1H), 4.02 (t, J=5.6 Hz, 2H), 2.70 (t, J=5.6 Hz, 2H), 2.29 (s, 6H), 2.24 (m, 1H), 1.75 (m, 1H) 0.80 (t, J=7.3 Hz, 3H); MS [ESI, (M+H)+] 406.

Example 6. Synthesis of 1-(4-(2-(dimethylamino)ethoxy)phenyl)-2-(4'-fluoro-[1,1'-biphenyl]-2-yl)pentan-1-one (MC-290298)

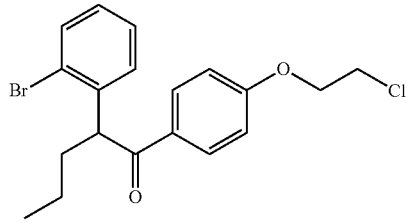 [SMILES: CCCC(C(=O)c1ccc(OCCCl)cc1)c1ccccc1Br]

Step 1. 2-(2-Bromophenyl)-1-(4-(2-chloroethoxy)phenyl)pentan-1-one

To a solution of 2-(2-bromo-phenyl)-1-(2-chloroethoxy)phenyl)ethan-1-one (2.0 g, 5.66 mmol) in dry tetrahydrofuran (25 mL) at room temperature was added sodium hydride (0.136 g, 5.67 mmol, 60% suspension in mineral oil) portionwise. After stirring 30 minutes, 1-iodopropane (0.58 mL, 6 mmol) was added via syringe. After 16 hours at 40° C., the mixture was poured into saturated aqueous ammonium chloride solution and extracted with diethyl ether (×2), dried over anhydrous magnesium sulfate and evaporated. The resulting residue was purified by chromatography on silica gel (gradient of ethyl acetate in hexane) to provide 1.2 g (54%) of the desired product as a clear oil. $^1$H NMR (400 MHz, CDCl$_3$) δ 7.90 (d, J=9.0 Hz, 2H), 7.50 (dd, J=8 Hz, J=1.1 Hz, 1H), 7.12 (m, 2H), 6.97 (m, 1H), 6.81 (d, J=9.0 Hz, 2H), 4.96 (dd, J=7.7 Hz, J=6.4 Hz, 1H), 4.17 (t, J=5.8 Hz, 2H), 3.73 (t, J=5.8 Hz, 2H), 2.04 (m, 1H), 1.63 (m, 1H), 1.35 (m, 1H), 1.21 (m, 1H), 0.86 (t, J=7.4 Hz, 3H); MS [ESI, (M+H)+] 397.

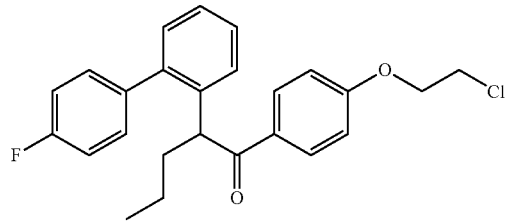 [SMILES: CCCC(C(=O)c1ccc(OCCCl)cc1)c1ccccc1-c1ccc(F)cc1]

Step 2. 1-(4-(2-Chloroethoxy)phenyl)-2-(4'-fluoro-[1,1'-biphenyl]-2-yl)pentan-1-one 2-(2-Bromophenyl)-1-(4-(2-chloroethoxy)phenyl)pentan-1-one (1.2 g, 3.04 mmol), 4-fluorophenylboronic acid (1.8 g, 12.94 mmol), anhydrous potassium fluoride (1.9 g, 32.7 mmol) and tris(dibenzylideneacetone)dipalladium(0) (0.280 g, 0.306 mmol) were added to a 40 mL vial fitted with a septa cap under nitrogen. The vial was sealed and purged with nitrogen for 5 minutes. Anhydrous tetrahydrofuran (5 mL) was added, and the mixture was purged for an additional 5 minutes. A solution of tri-tert-butylphosphine (10 wt % in hexanes; 2.72 mL, 0.918 mmol) was added via syringe, and the mixture was vigorously stirred at 60° C. for 16 hours. The mixture was diluted with 15 mL of ethyl acetate and filtered through a plug silica gel. The silica plug was washed with 50 mL of ethyl acetate and the combined filtrates were concentrated on a rotary evaporator to give a crude brown oil. The resulting residue was purified by chromatography on silica gel (gradient of ethyl acetate in hexane) to provide 0.620 g (50%) of the desired product as a white solid. $^1$H NMR (400 MHz, CDCl$_3$) δ 7.59 (d, J=9.0 Hz, 2H), 7.52 (dd, J=8 Hz, J=1.1 Hz, 1H), 7.33 (m, 3H), 7.24 (m, 4H), 6.81 (d, J=9.0 Hz, 2H), 4.82 (dd, J=8.9 Hz, J=5.2 Hz, 1H), 4.16 (t, J=5.6 Hz, 2H), 2.86 (t, J=5.4 Hz, 2H), 2.45 (t, J=5.4 Hz, 2H), 1.83 (m, 1H), 1.36 (m, 1H), 0.90 (t, J=7.9 Hz, 3H); MS [ESI, (M+H)+] 411.

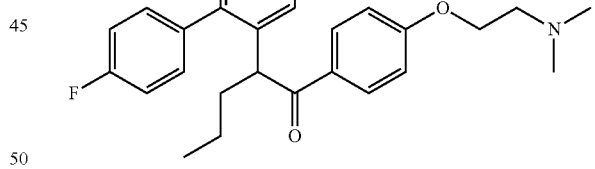

Step 3. 1-(4-(2-(Dimethylamino)ethoxy)phenyl)-2-(4'-fluoro-[1,1'-biphenyl]-2-yl)pentan-1-one 1-(4-(2-Chloroethoxy)phenyl)-2-(4'-fluoro-[1,1'-biphenyl]-2-yl)pentan-1-one (0.150 g, 0.36 mmol) was suspended in a mixture of 40% aqueous dimethylamine (10 mL) and ethanol (5 mL) and stirred at 65° C. 16 hours. The reaction mixture was cooled and then concentrated on a rotary evaporator. The resulting residue was dissolved in ethyl acetate, loaded onto a 4 g of silica gel column and eluted with 7 N ammonia in methanol (5%)/dichloromethane to provide crude title compound. The resulting oil was purified by reversed phase chromatography (gradient of acetonitrile in water with 0.1% trifluoroacetic acid modifier) to provide 100 mg (65%) of the desired product as a clear colorless oil (65%). $^1$H NMR (400 MHz, CDCl$_3$) δ 7.53 (d, J=8.9 Hz, 2H), 7.48 (dd, J=7.9 Hz, J=1.1 Hz, 1H), 7.24 (m, 7H), 6.8 (d, J=8.9 Hz, 2H), 4.64 (dd, J=9 Hz, J=5.1 Hz, 1H), 4.11 (t, J=5.6 Hz, 2H), 2.8 (t, J=5.6 Hz, 2H), 2.39 (s, 6H), 2.32 (m, 1H), 1.76 (m, 1H), 1.27 (m, 2H), 0.88 (t, J=7.3 Hz, 3H); MS [ESI, (M+H)+] 420.

Example 7. Synthesis of 2-(4'-fluoro-[1,1'-biphenyl]-2-yl)-1-(4-(2-(methylamino)ethoxy)phenyl)butan-1-one (MC-290291)

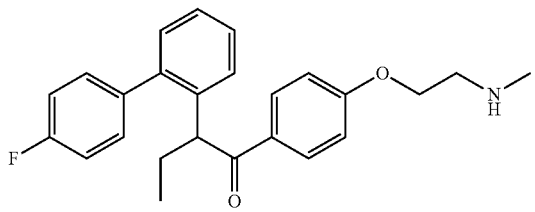 [SMILES: CCC(C(=O)c1ccc(OCCNC)cc1)c1ccccc1-c1ccc(F)cc1]

Step 1. 2-(4'-Fluoro-[1,1'-biphenyl]-2-yl)-1-(4-(2-(methylamino)ethoxy)phenyl)butan-1-one 1-(4-(2-Chloroethoxy)phenyl)-2-(4'-fluoro-[1,1'-biphenyl]-2-yl)butan-1-one (0.200 g, 0.51 mmol) was suspended in a mixture of 40% aqueous methylamine (5 mL) and ethanol (5 mL) and stirred at 65° C. 16 hours. The reaction mixture was cooled and then concentrated on a rotary evaporator. The resulting residue was dissolved in ethyl acetate and loaded onto a 4 g of silica gel column and eluted with 7 N ammonia in methanol (5%)/dichloromethane to provide crude title compound. The resulting oil was purified by reversed phase chromatography (gradient of acetonitrile in water with 0.1% trifluoroacetic acid modifier) to provide 35 mg of the desired product as a clear colorless oil (55%). $^1$H NMR (400 MHz, CDCl$_3$) δ 7.43 (d, J=8.9 Hz, 2H), 7.36 (dd, J=8 Hz, J=1.1 Hz, 1H), 7.13 (m, 7H), 6.67 (d, J=8.9 Hz, 2H), 4.42 (dd, J=9 Hz, J=5.1 Hz, 1H), 4.01 (t, J=5 Hz, 2H), 2.91 (t, J=5, 2H), 2.48 (s, 3H), 2.25 (m, 1H), 2.1 (bs, 1H), 1.75 (m, 1H), 0.81 (t, J=7.3 Hz, 3H); MS [ESI, (M+H)+] 392.

Example 8. Synthesis of 2-(4'-fluoro-[1,1'-biphenyl]-2-yl)-1-(4-(2-(methylamino)ethoxy)phenyl)pentan-1-one (MC-290299)

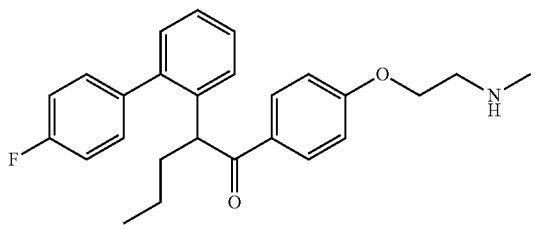 [SMILES: CCCC(C(=O)c1ccc(OCCNC)cc1)c1ccccc1-c1ccc(F)cc1]

Step 1. 2-(4'-Fluoro-[1,1'-biphenyl]-2-yl)-1-(4-(2-(methylamino)ethoxy)phenyl)pentan-1-one 1-(4-(2-Chloroethoxy)phenyl)-2-(4'-fluoro-[1,1'-biphenyl]-2-yl)pentan-1-one (0.150 g, 0.36 mmol) was suspended in a mixture of 40% aqueous dimethylamine (10 mL) and ethanol (5 mL) and stirred at 65° C. 16 hours. The reaction mixture was cooled and then concentrated on a rotary evaporator. The resulting residue was dissolved in ethyl acetate and loaded onto a 4 g of silica gel column and eluted with 7 N ammonia in methanol (5%)/dichloromethane to provide crude title compound. The resulting oil was purified by reversed phase chromatography (gradient of acetonitrile in water with 0.1% trifluoroacetic acid modifier) to provide 35 mg of the desired product as a clear colorless oil (68%). $^1$H NMR (400 MHz, CDCl$_3$) δ 7.53 (d, J=8.9 Hz, 2H), 7.48 (dd, J=8 Hz, J=1.1 Hz, 1H), 7.23 (m, 7H), 6.76 (d, J=8.9 Hz, 2H), 4.64 (dd, J=9 Hz, J=5.2 Hz, 1H), 4.1 (t, J=5.2 Hz, 2H), 3.0 (t, J=5.2, 2H), 2.51 (s, 3H), 2.32 (m, 1H), 2.1 (bs, 1H) 1.76 (m, 1H), 1.28 (m, 2H), 0.88 (t, J=7.3 Hz, 3H); MS [ESI, (M+H)+] 406.

Example 9. Synthesis of 2-(4'-fluoro-[1,1'-biphenyl]-2-yl)-4-methyl-1-(4-(2-(methylamino)-ethoxy)phenyl)pentan-1-one (MC-290288)

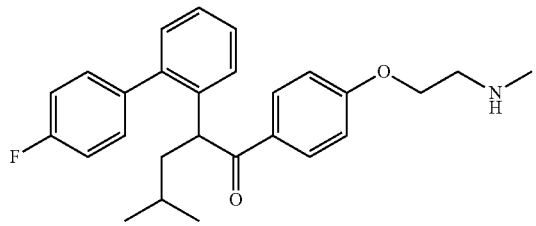 [SMILES: CNCCOc1ccc(C(=O)C(CC(C)C)c2ccccc2-c2ccc(F)cc2)cc1]

Step 1. 2-(4'-Fluoro-[1,1'-biphenyl]-2-yl)-4-methyl-1-(4-(2-(methylamino)ethoxy)phenyl)pentan-1-one 1-(4-(2-Chloroethoxy)phenyl)-2-(4'-fluoro-[1,1'-biphenyl]-2-yl)-4-methylpentan-1-one (0.150 g, 0.35 mmol) was suspended in a mixture of 40% aqueous methylamine (5 mL) and ethanol (5 mL) and stirred at 65° C. 16 hours. The reaction mixture was cooled and then concentrated on a rotary evaporator. The resulting residue was dissolved in ethyl acetate and loaded onto a 4 g of silica gel column and eluted with 7 N ammonia in methanol (5%)/dichloromethane to provide crude title compound. The resulting oil was purified by reversed phase chromatography (gradient of acetonitrile in water with 0.1% trifluoroacetic acid modifier) to provide 80 mg (54%) of the desired product as a clear colorless oil. $^1$H NMR (400 MHz, CDCl$_3$) δ 7.48 (d, J=8.9 Hz, 2H), 7.39 (dd, J=7.9 Hz, J=1.1 Hz, 1H), 7.12 (m, 7H), 6.8 (d, J=8.9 Hz, 2H), 4.65 (dd, J=9.4 Hz, J=4.2 Hz, 1H), 4 (t, J=5.2 Hz, 2H), 2.9 (t, J=5.2, 2H), 2.4 (s, 3H), 2.25 (m, 1H), 2.00 (bs, 1H), 1.44 (m, 2H), 0.76 (d, J=6.4 Hz, 3H), 0.69 (d, J=6.4 Hz, 3H); MS [ESI, (M+H)+] 420.

FORMULATIONS

The present invention also relates to compositions or formulations which comprise the functionalized N,N-dialkylamino phenyl ethers according to the present invention. In general, the compositions of the present invention comprise an effective amount of one or more functionalized N,N-dialkylamino phenyl ethers and salts thereof according to the present invention which are effective for treating and preventing diseases and conditions that involve lysosomal storage dysfunction, including, for example, Gaucher's disease, Tay-Sachs disease, Sandhoffs disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, and GM2 gangliosidosis; and one or more excipients. In addition, the compositions of the present invention comprise an effective amount of one or more functionalized N,N-dialkylamino phenyl ethers and salts thereof according to the present invention which are effective for treating and preventing diseases and conditions that involve misfolding of lysosomal related proteins and one or more excipients. Further, the compositions of the present invention comprise an effective amount of one or more functionalized N,N-dialkylamino phenyl ethers and salts thereof according to the present invention which are effective for treating and preventing Parkinson's disease and synucleinopathies dementia with Lewy bodies (DLB), pure autonomic failure (PAF), and multiple system atrophy (MSA). In addition, the compositions of the present invention comprise an effective amount of one or more functionalized N,N-dialkylamino phenyl ethers and salts thereof according to the present invention which are effective for treating and preventing fungal infections. Further, the compositions of the present invention comprise an effective amount of one or more functionalized N,N-dialkylamino phenyl ethers and salts thereof according to the present invention which are effective for treating and preventing diseases and conditions that involve calcium signaling dysfunction. Further, the compositions of the present invention comprise an effective amount of one or more functionalized N,N-dialkylamino phenyl ethers and salts thereof according to the present invention which are effective for treating and preventing diseases and conditions that involve β-glucocerebrosidase dysfunction. Further, the compositions of the present invention comprise an effective amount of one or more functionalized N,N-dialkylamino phenyl ethers and salts thereof according to the present invention which are effective for treating and preventing diseases and conditions that involve α-galactosidase A dysfunction. Further, the compositions of the present invention comprise an effective amount of one or more functionalized N,N-dialkylamino phenyl ethers and salts thereof according to the present invention which are effective for treating and preventing diseases and conditions that involve β-galactosidase dysfunction. Further, the compositions of the present invention comprise an effective amount of one or more functionalized N,N-dialkylamino phenyl ethers and salts thereof according to the present invention which are effective for treating and preventing diseases and conditions that involve β-hexosaminidase dysfunction. Further, the compositions of the present invention comprise an effective amount of one or more functionalized N,N-dialkylamino phenyl ethers and salts thereof according to the present invention which are effective for treating and preventing diseases and conditions that involve α-glucosidase dysfunction. Further, the compositions of the present invention comprise an effective amount of one or more functionalized N,N-dialkylamino phenyl ethers and salts thereof according to the present invention which are effective for treating and preventing diseases and conditions that involve N-acetylgalactosamine-4-sulfatase dysfunction. Further, the compositions of the present invention comprise an effective amount of one or more functionalized N,N-dialkylamino phenyl ethers and salts thereof according to the present invention which are effective for treating and preventing diseases and conditions that involve heparan sulfate acetyl-CoA dysfunction. Further, the compositions of the present invention comprise an effective amount of one or more functionalized N,N-dialkylamino phenyl ethers and salts thereof according to the present invention which are effective for treating and preventing diseases and conditions that involve α-glucosaminidine N-acetyltransferase dysfunction. Further, the compositions of the present invention comprise an effective amount of one or more functionalized N,N-dialkylamino phenyl ethers and salts thereof according to the present invention which are effective for treating and preventing diseases and conditions that involve galactocerebrosidase dysfunction. Further, the compositions of the present invention comprise an effective amount of one or more functionalized N,N-dialkylamino phenyl ethers and salts thereof according to the present invention which are effective for treating and preventing diseases and conditions that involve mucolipins 1 dysfunction. Further, the compositions of the present invention comprise an effective amount of one or more functionalized N,N-dialkylamino phenyl ethers and salts thereof according to the present invention which are effective for treating and preventing diseases and conditions that involve mucolipins 2 dysfunction. Further, the compositions of the present invention comprise an effective amount of one or more functionalized N,N-dialkylamino phenyl ethers and salts thereof according to the present invention which are effective for treating and preventing diseases and conditions that involve mucolipins 3 dysfunction.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known therapeutic agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more functionalized N,N-dialkylamino phenyl ethers according to the present invention and one or more excipients; from about 0.01 mg to about 100 mg of one or more functionalized N,N-dialkylamino phenyl ethers according to the present invention and one or more excipients; and from about 0.1 mg to about 10 mg of one or more functionalized N,N-dialkylamino phenyl ethers according to the present invention; and one or more excipients.

PROCEDURES

The following procedures can be utilized in evaluating and selecting compounds as therapeutic agents.

Phenotypic Assay: A phenotypic cellular assay utilizing lysosomal storage disorder (LSD) patient derived cells was developed to identify compounds with disease modifying activity to reverse or attenuate the disease phenotype to non-disease levels. The phenotypic assay was based on a functional readout we observed in cell lines derived from LSD disease patients reflective of the LSD diseased state. This functional readout of the LSD diseased state was developed into a high throughput screening assay.

Figure 3:
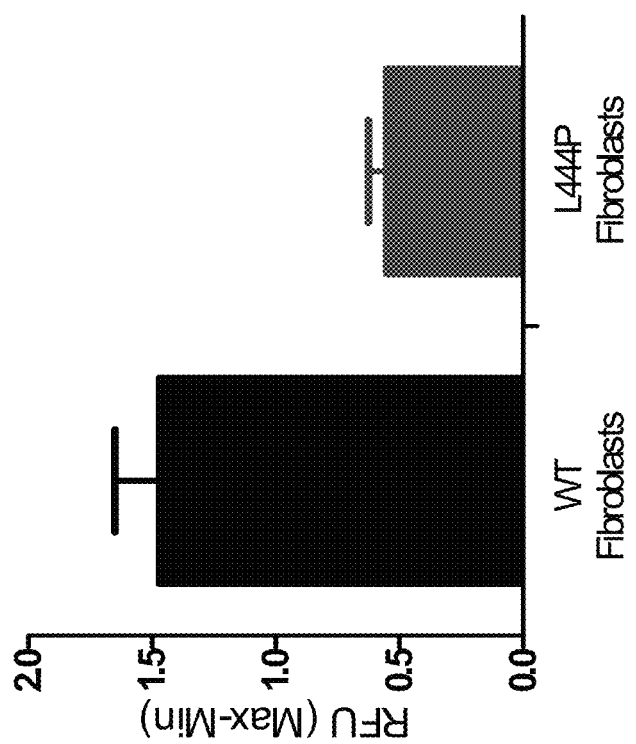
FIG. 3 is a graph of experimental data demonstrating that GPN-induced calcium release is reduced in GD L444P/L444P patient derived fibroblasts compared to normal fibroblasts (WT).
Figure 4:
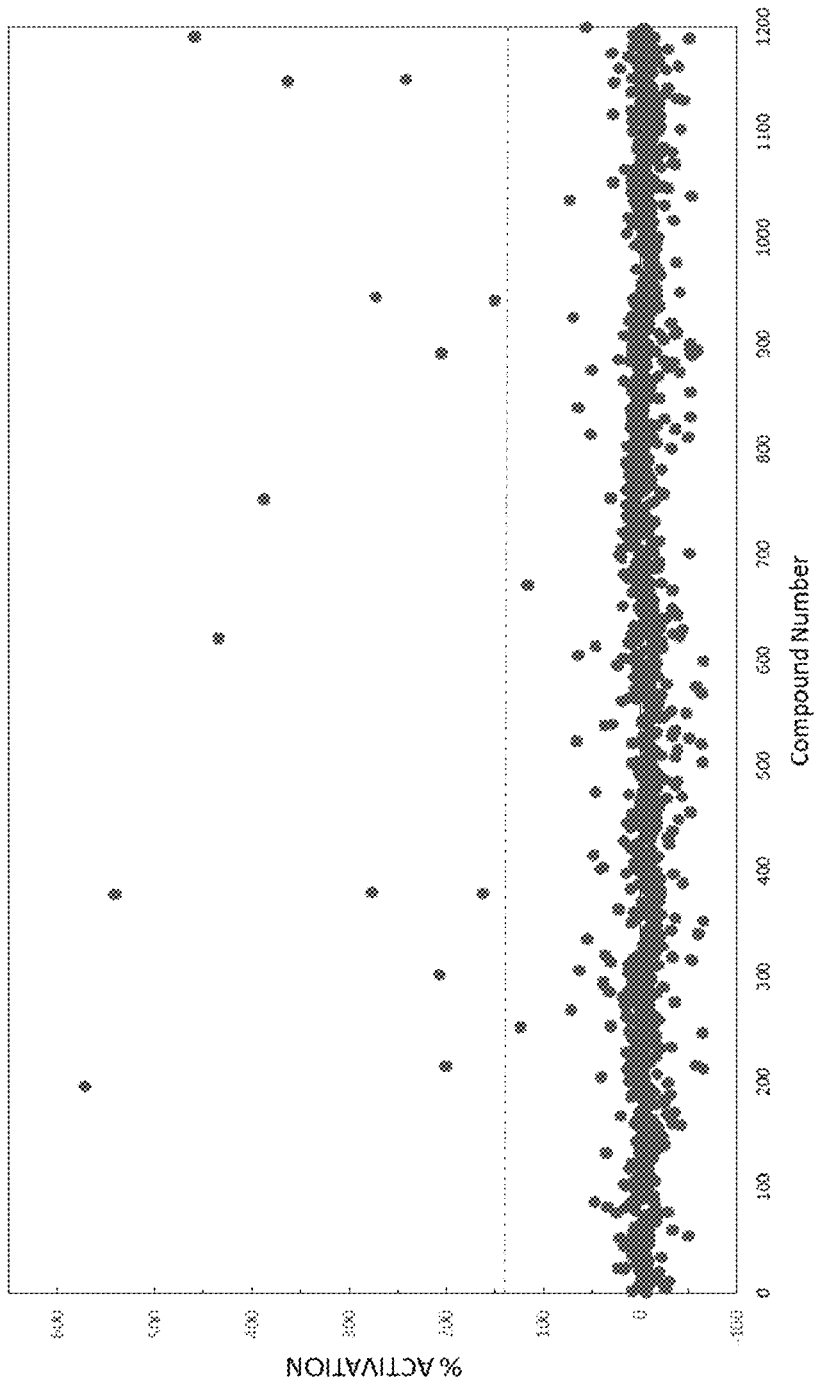
FIG. 4 is a graph of a Pilot HTS screen of Prestwick 1200 compound collection on L444P/L444P Gaucher patient phenotypic assay. Combined data of four 384-well plates. Dashed blue line is 3×SD of mean. Hits are points above 3×SD mean.
Figure 5:
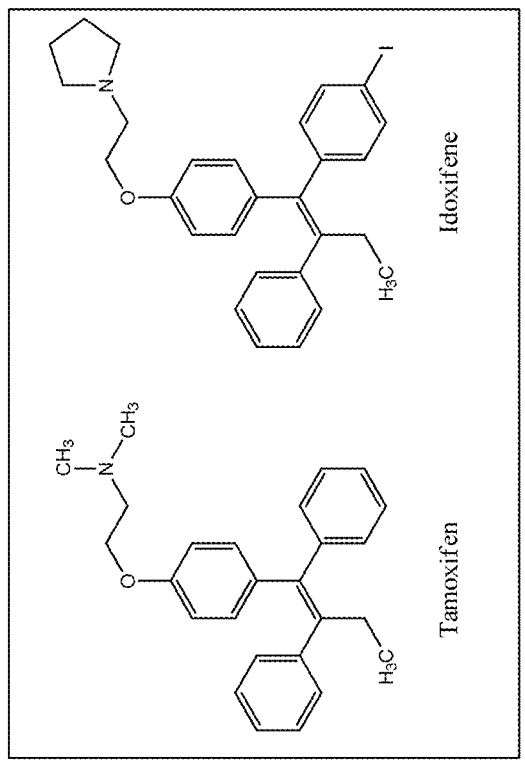
FIG. 5 depicts the structures of Tamoxifen and Idoxifen.

Disruption of lysosomal calcium homeostasis has been linked to the pathophysiology of lysosomal storage disorders including Gaucher disease (Lloyd-Evans, E, Morgan A J, He X, Smith D A, Elliot-Smith E, Sillence D J, Churchill G C, Schuchman E H, Galione A, Platt F M. (2008) Niemann-Pick disease type $C_1$ is a sphingosine storage disease that causes deregulation of lysosomal calcium. Nat Med. 14(11):1247-55. Lloyd-Evans E, Platt F M. (2011) Lysosomal Ca($2+$) homeostasis: role in pathogenesis of lysosomal storage diseases. Cell Calcium. 50(2):200-205. Morgan, A J, Platt, F M, Lloyd-Evans, E and Galione, A (2011) Molecular mechanism of endolysosomal $Ca^{2+}$ signaling in health and disease. Biochem. J. 439:349-374.). Calcium release from acidic lysosomal stores can be induced by addition of Gly-Phe-β-napthylamide (GPN), a substrate of cathepsin C, which upon hydrolysis, produces osmotic lysis of lysosomes and release of calcium specifically from lysosomal acidic stores into the cytosol. The increase of intracellular calcium released from lysosomes can be detected with cell membrane permeable calcium sensitive indicators. In comparison to fibroblasts from wild-type, non-affected patients, fibroblasts from wild-type, non-affected patients, fibroblasts derived from Gaucher disease L444P/L444P patients exhibit reduced release of calcium in response to GPN (FIG. 3). The reduction in lysosomal calcium release in comparison to normal, wild-type patient fibroblasts is a functional readout reflective of the LSD disease state and was further developed as the basis of a cellular, phenotypic assay to use for identifying compounds with activity to restore the LSD disease to normal.

Figure 6:
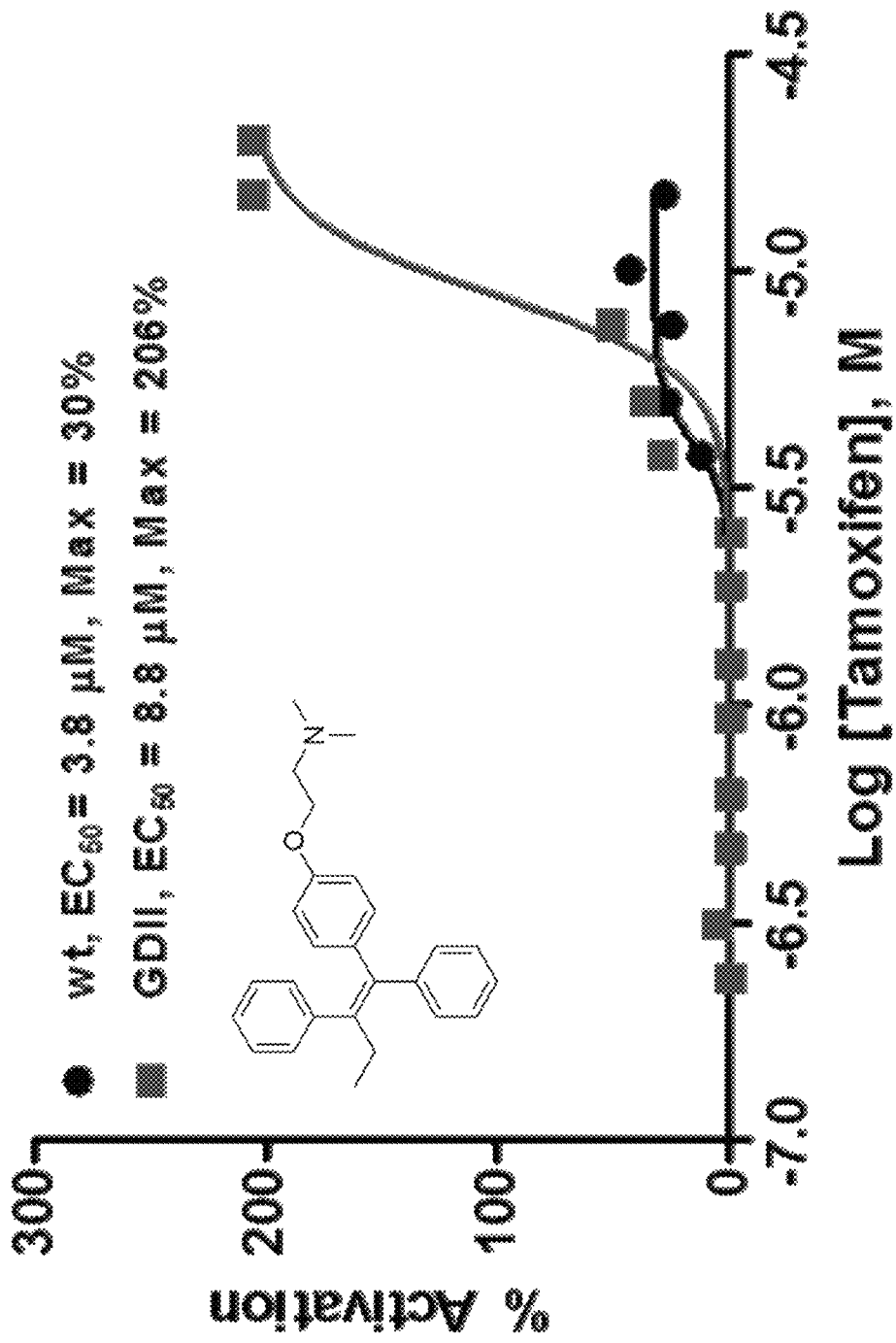
FIG. 6 is a graph of experimental data demonstrating the effect of tamoxifen on GPN-induced calcium release on wildtype and Gaucher L444P/L444P patient fibroblasts. % change in GPN response calculated as ratio of GPN response measured in presence of drug/GPN response in absence of drug X.

Identification of Tamoxifen as active in reversing LSD disease phenotype: The Prestwick Chemical Library®, a collection of 1200 known FDA approved drugs, was screened to identify compounds with activity to restore the LSD disease phenotype in Gaucher patient cells to normal levels. Cells (800 cells/well) were plated with a MultiFlo dispenser (BioTek) and cultured for 24 h at 37° C., 5% $CO_2$. The screening compounds were then added to cells under sterile conditions and continued in culture for 72 hours. Cells were loaded with Screen Quest™ Fluo-8 No Wash Calcium mix (ATT Bio) and analyzed for changes in response to GPN. The data from each well were normalized with basal fluorescence by dividing the maximum fluorescence over the entire real time reading by the initial basal fluorescence. Tamoxifen was identified as an active compound to increase lysosomal calcium signaling as a measure of disease phenotype reversal. The activity of Tamoxifen was confirmed in triplicate and the functional potency was determined on Gaucher patient and compared to wild type, normal patient cells. $EC_{50}$ and Hill slope values are determined using a four-parameter dose-response (variable slope) equation in GraphPad Prism. The % change in GPN response is calculated as the ratio of GPN response measured in the presence of drug/GPN response measured in the absence of drug×100. Tamoxifen exhibited $EC_{50}$=8.8±0.18 µM and 200±50% increase in calcium response compared with 0.1% DMSO treated Gaucher patient cells. The maximal % change in GPN response is calculated as the ratio of GPN response measured in the presence of drug/GPN response measured in the absence of drug×100. Tamoxifen also increased the GPN-induced response on wild type cells, $EC_{50}$=3.8±0.38 µM, however in comparison with Gaucher cells, the increase in GPN-induced calcium response was smaller (30+/−20%) (FIG. 6).

Gaucher patient fibroblasts (Coreill Institute, GM08760) were cultured in EMEM with 15% FBS, 1% Pen/Strep at 37° C./5% $CO_2$. Wild-type patient fibroblasts (Coriell Institute, GM 005659) were used as a control cell line. Cells are plated with a MultiFlo dispenser (800 cells/well in 30 µL of complete growth media) in black/clear bottom 384-well plates and cultured for 24 hours at 37° C., 5% $CO_2$. Compounds of the disclosure are then added to the cells (12 point dose response curve, 150 nM to 30 uM final compound concentration using a 5.0 µL of a 7× stock solution (1.05 µM to 210 µM)) under sterile conditions and continued in culture for 72 hours at 37° C., 5% $CO_2$. For intracellular calcium measurements, media is removed and 20 µL of calcium dye mixture (Screen Quest™ Fluo-8 No Wash Calcium mix, ATT Bioquest) is added to each well, incubated for 30 minutes at 37° C., followed by 22° C. for 30 minutes. Changes in fluorescence intensity are monitored on the FDSS µCell fluorescence kinetic plate reader, (excitation, 480 nm, emission 540 nm) reading at 1 Hz for a 20 seconds baseline followed by a 5 minute recording after addition of 50 µM GPN. The data from each well were normalized with basal fluorescence by dividing the maximum fluorescence over the entire real time reading by the initial basal fluorescence. Results are expressed as peak fluorescence change in relative fluorescence units (RFU).

Determination of the activity, $EC_{50}$ and % maximal response of synthesized analogs measured in Gaucher patient cells: The functional potency ($EC_{50}$) and % maximal activation of compounds of the disclosure were measured in the GPN induced calcium assay on Gaucher patient cells. A 12-point dilution curve in triplicate was prepared from serial dilution of 10 mM compounds stocks in 100% DMSO and added to Gaucher cells. After 72 hours, cells were loaded with Screen Quest™ Fluo-8 No Wash Calcium mix (ATT Bio) and analyzed for changes in response to GPN. The data from each well were normalized with basal fluorescence by dividing the maximum fluorescence over the entire real time reading by the initial basal fluorescence. The maximal % change in GPN response is calculated as the ratio of GPN response measured in the presence of drug/GPN response measured in the absence of drug×100.

TABLE 4

Functional potency ($EC_{50}$) and % maximal change in the GPN induced calcium release in Gaucher patient cells of representative compounds of the disclosure.

| Example | MC-number | Maximal % Change in GPN Response | $EC_{50}$ (µM) |
| --- | --- | --- | --- |
| 1 | 290042 | 250% | 3.6 |
| 2 | 290063 | 160% | 1.8 |
| 3 | 290284 | 400% | 0.185 |
| 4 | 290295 | 360% | 0.475 |
| 5 | 290290 | 630% | 0.266 |
| 6 | 290298 | 410% | 0.424 |
| 7 | 290291 | 515% | 0.425 |
| 8 | 290299 | 330% | 0.356 |
| 9 | 290288 | 617% | 0.236 |

β-Glucocerebrosidase Activity Enhanced in Gaucher Patient Cells after Tamoxifen and synthesized analog treatment: Gaucher patient fibroblasts were cultured for 3 days in 10 µM final concentration tamoxifen or synthesized analogs. Cellular lysates were prepared from compound treated cells and non-treated cells were included as a control. β-Glucocerebrosidase (GCase) activity was directly measured from lysates prepared from treated cells using a fluorescent substrate 4-methylumbelliferyl-β-D-glucopyranoside (MUG). Cells were washed 3× with phosphate-buffered saline (PBS) and detached by scraping. After centrifugation, The pellets were frozen on dry ice, thawed and lysed in McIlvaine (MI) buffer (100 mM sodium citrate, 200 mM sodium phosphate dibasic, 0.25% sodium taurocholate, and 0.1% Triton X-100, pH 5.2 containing protease inhibitors). Lysates are incubated with 3.0 mM 4-methylumbeliferryl-β-glucoside (4-MUG) substrate in MI buffer (50 µL) at 37° C. for 60 minutes. Reactions were stopped by addition of 0.4 M glycine, pH 10.6 (70 µL). Fluorescence was measured on a Clariostar plate reader (BMG Labtech) for one second per well using 355 nm excitation and 460 nm emission. Total protein was determined with the Bradford protein assay kit (BioRad) according to the manufacturer's instructions. The GCase activity measured after compound treatment is normalized to non-treated cells and expressed as relative activity where no change in GCAse activity is equal 1. Tamoxifen, at 10 µM produced a 1.3-fold increase in GCase activity measured from lysates prepared from Gaucher patient cells after 3 day treatment compared with vehicle only treated cell lysates.

Figure 7:
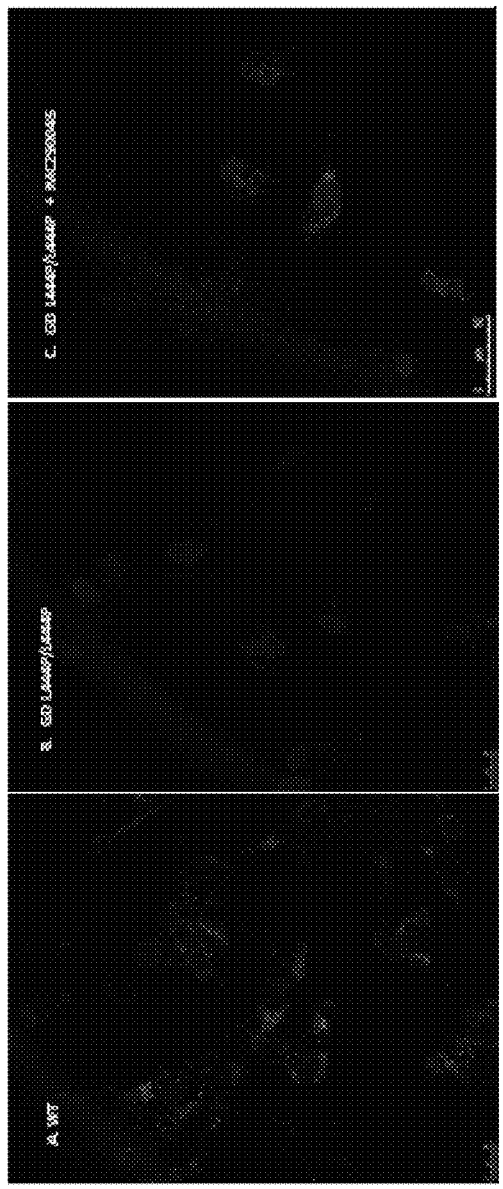
FIG. 7, comprising
Figure 7:
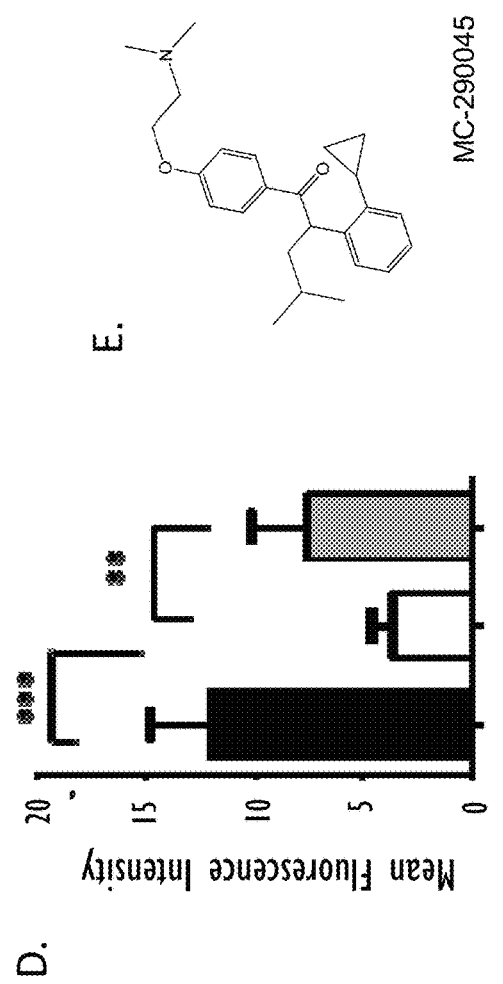

In Gaucher disease, severely reduced or lack of GCase activity resulting from mutations produce misfolded enzyme with inability to traffic to the lysosome. This is hypothesized to contribute to the impaired lysosomal function and increased accumulation glucosylceramide (Grabowski, 2012, Hematology Am. Soc. Hematol. Educ. Program 2012: 13-18). Normalization of dysfunctional calcium homeostasis has been shown to improve GCase folding and trafficking in Gaucher patient fibroblasts and restore lysosomal function (Wang et al. 2011, ACS Chem. Biol. 6:158-168; Mu et al., 2008, PLoS Biol. 6:226; Ong et al., 2010, Nat. Chem. Biol. 6:424-432). Lysosomal GCase can be detected with the fluorescence probe MDW933, specific for active lysosomal enzyme by labeling active enzyme in vitro in cultured cells and quantitation with confocal microscopy (Witte et al., 2010, Nat. Chem. Biol. 6:907-913; Jian et al., 2016, EBioMedicine 13:212-224). MDW933 labeling was used as an orthogonal assay to assess efficacy of analogs to produce enhanced GCase activity in Gaucher L444P/L444P (FIG. 7). GD L444P/L444P fibroblasts show 5-fold reduced GCase levels compared to wild-type fibroblasts with MDW933 labeling, consistent with low activity measured in enzymatic assays on cell lysates. Gaucher L444P/L444P cells treated for 72 hour with 5 µM MC-290045, showed 2-fold increase in GCase activity compared with vehicle treated cells.

Antifungal activity assay to determine MIC and MFC: Antifungal activity of the compounds of the disclosure may be evaluated using USA standards, Clinical and Laboratory Standards Institute (CLSI) criteria. In brief, inocula from 24 hour *Candida* cultures on Sabouraud's dextore agar are standardized to a turbidity equivalent of 0.5 McFarland standards at 520 nm with a spectrophotometer. The suspensions are further diluted in Rosewell Park Memorial Institute (RPMI) 1640 medium (Life technologies, New York, USA) to yield an inoculum concentration of approximately 0.5 1×10³ to 2.5 1×10³ Cells/ml. Minimum inhibitory concentration (MIC) and minimum fungicidal concentration (MFC) assay are performed in 96-well plates and *Candida* species are exposed to a double dilution of compounds of the disclosure. Amphotericin B may be used as a positive control. All the experiments are preformed three times with duplicates. The plates are incubated at 35° C. for 48 hours to evaluate MIC.

Antifungal activity assay against biofilm: Antifungal activity of compounds of the disclosure may be determined using sessile cells of an appropriate species. Isolates may be propagated in yeast peptone dextrose (YPD) medium (1% (wt/vol) yeast extract, 2% (wt/vol) peptone, 2% (wt/vol) dextrose). Flasks containing liquid medium (20 ml) may be inoculated with a loopful of cells from YPD agar plates containing freshly grown isolates and incubated overnight in an orbital shaker (100 rpm) at 30° C. Strains grow in the budding yeast phase under these conditions. Cells may be harvested and washed in sterile phosphate-buffered saline (PBS; 10 mM phosphate buffer, 2.7 mM potassium chloride, 137 mM sodium chloride (pH 7.4)). Cells may re-suspended in RPMI 1640 supplemented with 1-glutamine and buffered with morpholinepropanesulfonic acid to a cellular density equivalent to 1.0×10⁶ cells per ml. Biofilms may be formed on commercially available presterilized, polystyrene, flat-bottom 96-well microtiter plates by pipetting standardized cell suspensions (100 µl of the 10⁶ cells/ml) into selected wells of the microtiter plate and incubating them for 48 hours at 37° C. After biofilm formation, the medium may be aspirated and non-adherent cells removed by thoroughly washing the biofilms three times in sterile PBS. Residual PBS may be removed by blotting with paper towels before the addition of compounds of the disclosure in serially double-diluted concentrations (1,024 to 1 g/ml and 32 to 0.125 g/ml, respectively, from stock solutions of each antifungal agent prepared in RPMI medium directly) and incubated for a further 48 h at 35° C. A series of antifungal agent-free wells and biofilm-free wells were also included to serve as positive and negative controls, respectively. Sessile MICs (SMICs) were determined at 50 and 80% inhibition $SMIC_{50}$ and $SMIC_{80}$, respectively) by using the XTT reduction assay.

XTT-reduction assay: A semiquantitative measure of biofilm formation are calculated by using an XTT [2,3-bis(2-methoxy-4-nitro-5-sulfo-phenyl)-2H-tetrazolium-5-carboxanilide]-reduction assay. Briefly, XTT is prepared in a saturated solution at 0.5 g/liter in Ringer's lactate. The solution is filter sterilized through a 0.22-µm-pore-size filter, aliquoted, and stored at −70° C. Prior to each assay, an aliquot of stock XTT is thawed, and menadione (10 mM prepared in acetone) is added to a final concentration of 1 µM. A 100-µl aliquot of the XTT-menadione solution is then added to each prewashed biofilm and to control wells (for the measurement of background XTT-reduction levels). The plates are incubated in the dark for 2 hours at 37° C. A colorimetric change in the XTT-reduction assay, a direct correlation of the metabolic activity of the biofilm, is then measured in a microtiter plate reader at 490 nm.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound having formula (I):

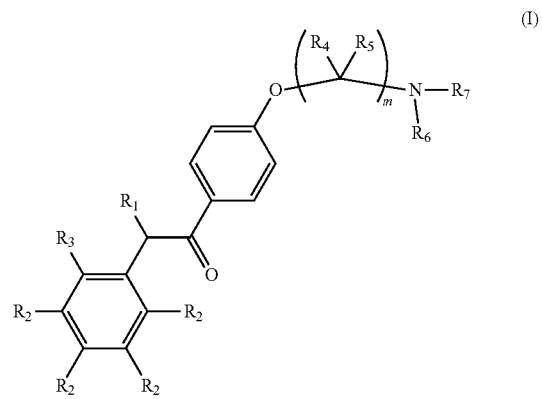

Including enantiomers, diastereomers, hydrates, solvates, pharmaceutically acceptable salts, prodrugs and complexes thereof, wherein:

$R^1$ is selected from the group consisting of hydrogen, $C_1$-$C_6$ linear alkyl, $C_1$-$C_{10}$ branched alkyl, alkenyl, alkynyl, $C_3$-$C_{10}$ cycloalkyl, cycloalkenyl, alkyl-cycloalkyl and alkyl-cycloalkenyl optionally substituted with a $C_1$-$C_5$ alkyl group;

$R^2$ is at each occurrence independently selected from the group consisting of H, OH, halogen, CN, $NO_2$, $C_1$-$C_{10}$ alkoxy, $C_3$-$C_{10}$ branched alkoxy, $C_1$-$C_{10}$ haloalkoxy, $C_3$-$C_{10}$ branched haloalkoxy, $NR^8R^9$, $C(O)OR^{10}$, $C_1$-$C_{10}$ thioalkyl, $C_3$-$C_{10}$ branched thioalkyl, $C_1$-$C_{10}$ halothioalkyl, —$S(O)C_1$-$C_{10}$ alkyl, —$S(O)C_3$-$C_{10}$ branched alkyl, —$S(O)C_1$-$C_{10}$ haloalkyl, —$S(O)C_3$-$C_{10}$ branched haloalkyl, —$SO_2C_1$-$C_{10}$ alkyl, —$SO_2C_3$-$C_{10}$ branched alkyl, —$SO_2C_1$-

$C_{10}$ haloalkyl, —$SO_2C_1$-$C_{10}$ branched haloalkyl, $SO_2NR^{11}R^{12}$, —$NR^{11}SO_2R^{13}$, $C(O)$—$NR^{11}R^{12}$;

$R^3$ is a substituted or unsubstituted aryl or heteroaryl group of 1-10 carbon atoms, wherein the heteroaryl group comprises 1-4 heteroatoms, wherein the heteroatom is selected from the group consisting of O, N, S, S(O), $SO_2$, and wherein the aryl or heteroaryl group may be optionally substituted with a substituent selected from the group consisting of H, OH, halogen, CN, $NO_2$, $C_1$-$C_{10}$ alkoxy, $C_3$-$C_{10}$ branched alkoxy, $C_1$-$C_{10}$ haloalkoxy, $C_3$-$C_{10}$ branched haloalkoxy, $NR^8R^9$, $C(O)OR^{10}$, $C_1$-$C_{10}$ thioalkyl, $C_3$-$C_{10}$ branched thioalkyl, $C_1$-$C_{10}$ halothioalkyl, —$S(O)C_1$-$C_{10}$ alkyl, —$S(O)C_3$-$C_{10}$ branched alkyl, —$S(O)C_1$-$C_{10}$ haloalkyl, —$S(O)C_3$-$C_{10}$ branched haloalkyl, —$SO_2C_1$-$C_{10}$ alkyl, —$SO_2C_3$-$C_{10}$ branched alkyl, —$SO_2C_1$-$C_{10}$ haloalkyl, —$SO_2C_1$-$C_{10}$ branched haloalkyl, $SO_2NR^{11}R^{12}$, —$NR^{11}SO_2R^{13}$, $C(O)$—$NR^{11}R^{12}$;

$R^4$ is at each occurrence independently selected from the group consisting of hydrogen, $C_1$-$C_6$ linear alkyl, and $C_3$-$C_7$ branched alkyl;

$R^5$ is at each occurrence independently selected from the group consisting of hydrogen, $C_1$-$C_6$ linear alkyl, and $C_3$-$C_7$ branched alkyl;

m is 2, 3, 4, 5, 6, 7, 8, 9, or 10;

$R^6$ is selected from the group consisting of hydrogen, $C_1$-$C_6$ linear alkyl and $C_3$-$C_7$ branched alkyl;

$R^7$ is selected from the group consisting of hydrogen, $C_1$-$C_6$ linear alkyl and $C_3$-$C_7$ branched alkyl; or $R^6$ and $R^7$ may optionally be taken together with the atoms to which they are bound to form a ring containing 4 to 7 members, and wherein the ring may optionally comprise a member selected from the group consisting of O, S, and $NR^{14}$;

$R^8$ is at each occurrence independently selected from the group consisting of hydrogen, $C_1$-$C_6$ linear alkyl, and $C_3$-$C_7$ branched alkyl;

$R^9$ is at each occurrence independently selected from the group consisting of hydrogen, $C_1$-$C_6$ linear alkyl, and $C_3$-$C_7$ branched alkyl;

$R^{10}$ is at each occurrence independently selected from the group consisting of hydrogen, $C_1$-$C_6$ linear alkyl, and $C_3$-$C_7$ branched alkyl;

$R^{11}$ is at each occurrence independently selected from the group consisting of hydrogen, $C_1$-$C_6$ linear alkyl, and $C_3$-$C_7$ branched alkyl;

$R^{12}$ is at each occurrence independently selected from the group consisting of hydrogen, $C_1$-$C_6$ linear alkyl, and $C_3$-$C_7$ branched alkyl;

$R^{13}$ is at each occurrence independently selected from the group consisting of hydrogen, $C_1$-$C_6$ linear alkyl, and $C_3$-$C_7$ branched alkyl; and $R^{14}$ is at each occurrence independently selected from the group consisting of hydrogen, $C_1$-$C_6$ linear alkyl, and $C_3$-$C_7$ branched alkyl.

2. The compound of claim 1, wherein the compound of formula (I) is a compound of formula (II)

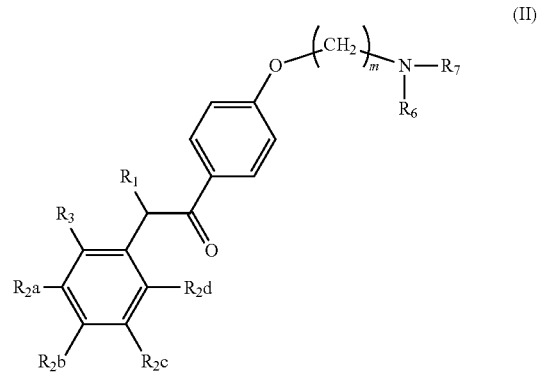

(II)

Including enantiomers, diastereomers, hydrates, solvates, pharmaceutically acceptable salts, prodrugs and complexes thereof.

3. The compound of claim 1, wherein the compound of formula (I) is a compound of formula (III)

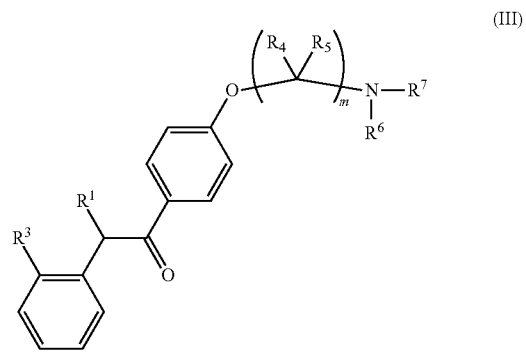

(III)

Including enantiomers, diastereomers, hydrates, solvates, pharmaceutically acceptable salts, prodrugs and complexes thereof.

4. The compound of claim 1, wherein the compound of formula (I) is a compound of (IV)

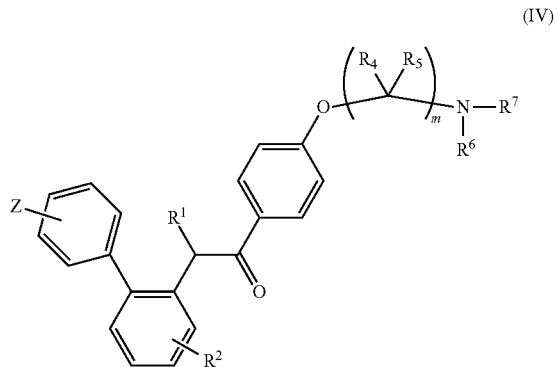

(IV)

Including enantiomers, diastereomers, hydrates, solvates, pharmaceutically acceptable salts, prodrugs and complexes thereof.

5. The compound of claim 1, wherein the compound of formula (I) is selected from the group consisting of:
2-([1,1'-Biphenyl]-2-yl)-1-(4-(dimethylamino)-ethoxy)phenyl)ethenone,
1-(4-(2-(Dimethylamino)ethoxy)phenyl)-2-(4'-fluoro-[1,1'-biphenyl]-2-yl)ethenone,
1-(4-(2-(Dimethylamino)ethoxy)phenyl)-2-(4'-fluoro-2'-methyl-[1,1'-biphenyl]-2-yl)ethenone,
1-(4-(2-(Dimethylamino)ethoxy)phenyl)-2-(4'-fluoro-3'-methyl-[1,1'-biphenyl]-2-yl)ethenone,
2-(2'-Chloro-[1,1'-biphenyl]-2-yl)-1-(4-(2-(dimethylamino)ethoxy)phenyl)ethenone,
1-(4-(2-(Dimethylamino)ethoxy)phenyl)-2-(3'-(trifluoromethyl)-[1,1'-biphenyl]-2-yl)ethenone,
1-(4-(2-(Dimethylamino)ethoxy)phenyl)-2-(4'-fluoro-2'-methoxy-[1,1'-biphenyl]-2-yl)ethenone,
1-(4-(2-(Dimethylamino)ethoxy)phenyl)-2-(3'-fluoro-4'-methoxy-[1,1'-biphenyl]-2-yl)ethenone,
2-(2',4'-Difluoro-[1,1'-biphenyl]-2-yl)-1-(4-(2-((dimethylamino)ethoxy)phenyl)ethenone,
1-(4-(2-(Dimethylamino)ethoxy)phenyl)-2-(3'-cyano-[1,1'-biphenyl]-2-yl)ethenone,
1-(4-(2-(Dimethylamino)ethoxy)phenyl)-2-(2'-fluoro-[1,1'-biphenyl]-2-yl)ethenone,
1-(4-(2-(Dimethylamino)ethoxy)phenyl)-2-(2'-(trifluoromethoxy)-[1,1'-biphenyl]-2-yl)ethenone,
1-(4-(2-(Dimethylamino)ethoxy)phenyl)-2-(4'-fluoro-5-(trifluoromethyl)-[1,1'-biphenyl]-2-yl)ethenone,
1-(4-(2-(Dimethylamino)ethoxy)phenyl)-2-(4'-fluoro-[1,1'-biphenyl]-2-yl)-4-methylpentan-1-one,
2-(2-cyclopropylphenyl)-1-(4-(2-(dimethylamino)ethoxy)phenyl)-4-methylpentan-1-one,
1-(4-(2-(dimethylamino)ethoxy)phenyl)-2-(4'-fluoro-[1,1'-biphenyl]-2-yl)-4-methylpentan-1-one,
3-cyclopropyl-1-(4-(2-(dimethylamino)ethoxy)phenyl)-2-(4'-fluoro-[1,1'-biphenyl]-2-yl)propan-1-one,
1-(4-(2-(dimethylamino)ethoxy)phenyl)-2-(4'-fluoro-[1,1'-biphenyl]-2-yl)butan-1-one,
1-(4-(2-(dimethylamino)ethoxy)phenyl)-2-(4'-fluoro-[1,1'-biphenyl]-2-yl)pentan-1-one,
2-(4'-fluoro-[1,1'-biphenyl]-2-yl)-1-(4-(2-(methylamino)ethoxy)phenyl)butan-1-one,
2-(4'-fluoro-[1,1'-biphenyl]-2-yl)-1-(4-(2-(methylamino)ethoxy)phenyl)pentan-1-one, and
2-(4'-fluoro-[1,1'-biphenyl]-2-yl)-4-methyl-1-(4-(2-(methylamino)-ethoxy)phenyl)pentan-1-one.

6. A composition comprising at least one compound according to claim 1 and at least one excipient.

7. A method for treating or preventing a disease or conditions that involve lysosomal storage dysfunction, said method comprising administering to a subject in need thereof an effective amount of at least one compound according to claim 1.

8. The method of claim 7, wherein the disease or conditions that involve lysosomal storage dysfunction is Gaucher's disease, Tay-Sachs disease, Sandhoff's disease, Sandhoff-Jatzkewitz disease, Fabry disease, Niemann Pick disease Type C, Pompe disease, type III A mucopolysaccharidosis, Sanfilippo syndrome, α-mannosidosis, GM1 gangliosidosis, or GM2 gangliosidosis.

9. The method of claim 7, wherein the at least one compound is administered in a composition further comprising at least one excipient.

10. A method of treating or preventing a fungal infection, said method comprising administering to a subject in need thereof an effective amount of at least one compound according to claim 1.

11. The method of claim 10, wherein the at least one compound is administered in a composition further comprising at least one excipient.

12. A method of treating or preventing Parkinson's disease, said method comprising administering to a subject in need thereof an effective amount of at least one compound according to claim 1.

13. The method of claim 12, wherein the at least one compound is administered in a composition further comprising at least one excipient.

14. A method of treating a synucleinopathy, said method comprising administering to a subject in need thereof an effective amount of at least one compound according to claim 1.

15. The method of claim 14, wherein the at least one compound is administered in a composition further comprising at least one excipient.

16. The method of claim 14, wherein the synucleinopathy is dementia with Lewy bodies (DLB), pure autonomic failure (PAF), or multiple system atrophy (MSA).

* * * * *